US007461649B2

(12) United States Patent
Gamard et al.

(10) Patent No.: US 7,461,649 B2
(45) Date of Patent: Dec. 9, 2008

(54) PORTABLE GAS OPERATING INHALER

(75) Inventors: Stephan C. F. Gamard, Buffalo, NY (US); Bryan R. Bielec, Hamburg, NY (US); Royce S. Fishman, Hernando, FL (US); Alan Cheng, Naperville, NY (US)

(73) Assignee: Praxair Technology, Inc., Danbury, CT (US)

( * ) Notice: Subject to any disclaimer, the term of this patent is extended or adjusted under 35 U.S.C. 154(b) by 375 days.

(21) Appl. No.: 10/845,411

(22) Filed: May 14, 2004

(65) Prior Publication Data

US 2005/0123483 A1 Jun. 9, 2005

Related U.S. Application Data

(63) Continuation-in-part of application No. 10/726,627, filed on Dec. 4, 2003.

(51) Int. Cl.
*A61M 11/00* (2006.01)
*A61M 15/00* (2006.01)
*A61M 16/00* (2006.01)

(52) U.S. Cl. ........................... 128/200.22; 128/200.11; 128/200.14; 128/203.12; 128/203.15; 128/204.18

(58) Field of Classification Search ............ 128/200.11, 128/200.12, 200.13, 200.14, 200.16, 200.23, 128/200.24, 203.12, 203.15, 204.18
See application file for complete search history.

(56) References Cited

U.S. PATENT DOCUMENTS 3,640,436 A 2/1972 Gallagher .............. 222/402.24
3,651,997 A 3/1972 Venus, Jr. .............. 222/402.16
4,271,865 A 6/1981 Galloway et al. ...... 137/614.06
4,380,505 A 4/1983 Wittenhorst
4,773,562 A * 9/1988 Gueret ....................... 222/135
5,304,125 A 4/1994 Leith
5,561,983 A 10/1996 Remes et al. ................ 62/48.1
5,711,292 A 1/1998 Hammarlund
5,724,986 A 3/1998 Jones, Jr. et al.

(Continued)

FOREIGN PATENT DOCUMENTS

EP 1110547 A2 6/2001

(Continued)

OTHER PUBLICATIONS

Gluck, et al., "Heulium-Oxygen Mixtures in Intubated Patients with Status Asthmaticus and Respiratory Acidosis", *Chest/98/3/*Sep. 1990, p. 693-698.

(Continued)

*Primary Examiner*—Justine R Yu
*Assistant Examiner*—Annette F Dixon
(74) *Attorney, Agent, or Firm*—Robert J. Hampsch

(57) ABSTRACT

An inhaler comprising a compressed gas, such as Heliox gas is provided. The disclosed inhaler includes a first chamber containing a compressed gas which is in communication with an equalization chamber having pressure lower than the pressure of the gas in the first chamber. The inhaler also includes a drug storage chamber which is detachably coupled to the equalization chamber and operable such that a portion of the compressed gas from the equalization chamber fluidizes and aerosolizes the drug to produce a drug cloud. The drug cloud is directed into a spacer where it can be inhaled by a user.

33 Claims, 9 Drawing Sheets

U.S. PATENT DOCUMENTS

| | | | |
|---|---|---|---|
| 5,839,430 A | 11/1998 | Cama | |
| 6,014,972 A * | 1/2000 | Sladek | 128/203.12 |
| 6,086,376 A | 7/2000 | Moussa et al. | 434/45 |
| 6,125,844 A * | 10/2000 | Samiotes | 128/200.23 |
| 6,352,684 B1 | 3/2002 | Purewal et al. | 424/45 |
| 6,698,422 B2 * | 3/2004 | Fugelsang et al. | 128/200.14 |
| 6,871,526 B2 * | 3/2005 | Tse et al. | 73/52 |
| 6,948,495 B2 | 9/2005 | Seppälä | |
| 2003/0146242 A1* | 8/2003 | Peterson | 222/137 |
| 2003/0199594 A1* | 10/2003 | Shah | 516/1 |
| 2003/0205227 A1 | 11/2003 | Hodson et al. | |
| 2004/0025875 A1 | 2/2004 | Reber et al. | |
| 2004/0129270 A1* | 7/2004 | Fishman | 128/204.18 |
| 2004/0234610 A1* | 11/2004 | Hall et al. | 424/489 |
| 2005/0123483 A1 | 6/2005 | Gamard et al. | |

FOREIGN PATENT DOCUMENTS

| | | |
|---|---|---|
| WO | WO 9955600 | 11/1999 |
| WO | WO 0078286 A1 | 12/2000 |
| WO | WO 03/049791 | 6/2003 |

OTHER PUBLICATIONS

"Inhalation Drug Delivery" *3M Drug Delivery Systems*.

Claudia Kalb and Jamie Reno, "From Needle to Nose" *Newsweek*, May 12, 2002.

* cited by examiner

PORTABLE GAS OPERATING INHALER

This is a Continuation-in-part of prior application Ser. No. 10/726,627 filed Dec. 4, 2003.

FIELD OF THE INVENTION

This invention relates to the field of inhalers used to administer a drug to a patient through the patient's lungs and, more particularly, to an improved gas inhaler.

BACKGROUND OF THE INVENTION

Definitions

As used herein, "Heliox" is defined as a gas mixture of helium and oxygen whose physical properties are summarized in Table 1 depending on the concentration of Helium.

TABLE 1

Physical properties of Heliox at 273 K, 1 atmosphere.

| | Percentage of Helium | | | | | |
|---|---|---|---|---|---|---|
| | 0 | 20 | 40 | 60 | 80 | 100 |
| Density (g/L) | 1.429 | 1.179 | 0.929 | 0.679 | 0.429 | 0.179 |
| Viscosity (µP) | 204 | 201.2 | 198.4 | 195.6 | 192.8 | 190 |
| Kinematic Viscosity (µm$^2$·s$^{-1}$) | 14.3 | 17.1 | 21.4 | 28.8 | 44.9 | 106.1 |

As used herein, "ambient air" is defined as that air which normally exists around us which is either inhaled and exhaled from the environment, or, pumped into a mechanical hand held device from the environment and then inhaled.

As used herein, "aerosolization" is primarily defined as the generation and then breakup of a liquid sheet into primary and satellite droplets, generally 1 micron to 20 microns in size, although the physical form of particles in an aerosol as used herein may be liquid drops or solid dry powder particles.

As used herein, "fluidization" is defined as the deagglomeration of a compact mass of drug in micronized dry powder form manufactured with a preferred particle size range of 1 micron to 5 microns into a cloud, with the objective being the generation of particles in the preferred 1-10 micron range, and more preferably in the 1-3 micron range.

As used herein, "heterodisperse aerosol" or "heterodisperse particle cloud" shall be defined as a deliverable form of a liquid drug formulation or dry powder drug formulation, such that there are particles of many different sizes.

As used herein, "monodisperse aerosol" or "monodisperse particle cloud" shall be defined as a deliverable form of a liquid drug formulation or dry powder drug formulation, such that the particles are all the same, or very near the same size.

As used herein, "alveoli" are air sacs deep in the lung at the terminal end of the smallest and last branch of bronchioles, where gas exchange takes place between the airspace in the lungs and arterial blood. Small particulate drug matter can enter the alveolar spaces, depending on their size and deposition characteristics. After entering the alveoli, the drug matter becomes engulfed by alveolar macrophages, which exist around each alveolus under its surfactant layer and enter the acinus by way of the terminal bronchiolar lumen. Drug particles may be absorbed from the lung primarily by alveolar macrophages.

As used herein, "fine particle dose" shall mean particles that are preferably about 5 µm or less, generally 3 µm or less, and more preferably 2 µm or less.

As used herein, "respirable fraction" (RF) is a dose fraction of aerosolized drug particles small enough in diameter to escape the filtration machinery of the airways and be deposited in the lungs.

As used herein, the terms "dry powder formulation" and "liquid formulation" are pharmacologically active drug by itself, or with any of the following including but not limited to propellants, carriers, excipients, surfactants, anti-microbial, flavoring, and other additions to the formulation that enhance production, shelf life stability, generation of particles, delivery to the desired site in the lungs, and absorption, macrophage or other processed base transfer from the air space into the tissue and blood, or taste.

General Medical Background

Delivery of therapeutic drugs via the lungs for respiratory and non-respiratory systemic diseases, is increasingly being recognized as a viable if not superior alternative to administration of drugs orally/nasally, rectally, transdermally, by intravenous needle injection, intra-muscular needle injection, or gas jet driven non-needle injection through the skin and into the muscle.

Around 1 million patients in the US receive intravenous morphine for the relief of chronic and terminal pain. Morphine actually acts more rapidly with respect to pain management when inhaled than when injected. In addition, there is a major effort to move away from CFC or other vapor pressure based propellant driven inhalers toward alternative technology, due to environmental issues.

All but oral and rectal modes of administration, ideally require a liquid form of drug. Hard particulate drug forms are being explored for gas jet driven needle-less injection through the skin for deposit into the muscle for extended or timed release of the drug substance.

In each of these non-pulmonary methods of drug administration, far higher doses of drug substance than that required for actual therapeutic effectiveness on the target system must be administered to assure that the required therapeutic amount of drug substance is actually delivered to the target system or site. This represents a risk factor to the patient, in that there is a therapeutic variable regarding the amount of dose delivered to the target system or site. The exception is where that target is very local to the site of administration (i.e., mouth, colon, patch of skin, area of muscle, etc).

In addition, many new drugs being developed by companies in the biotechnology field based on peptides and proteins, exist as dry powder in their optimum and/or most stable form, and so these drugs cannot be injected using a needle or needle-less method, or administered transdermally. Genetically produced peptide and protein based drugs are also very sensitive to being altered by in-vivo environmental factors such as enzymes and acids.

If such sensitive drug molecules in dry powder form are delivered orally, they are subjected to the enzymes and acids in the digestive tract. This can reduce the quantity of these sensitive therapeutic molecules available for absorption into the blood in their original therapeutic structure, increasing the need to initially deliver a higher oral dose. Rectal drug administration is neither pleasant, socially acceptable, or commercially viable except in extreme cases where no other choice exists.

The intravenous needle method of administering therapeutic drugs in liquid form in the arm or femorally, results in the dilution and loss of administered drug potency as the blood passes through the venous system back to the heart, then to the lungs, and finally into the arterial circulation for delivery.

Intra-muscular needle injection adds a pathway where part of the administered dose can be lost. The same is true for a gas driven jet needle-less injection, where the drug substance must go through the skin, into the muscle, (usually and primarily) into the venous blood system, and then into the arterial system.

Hence, it is necessary to inject more drugs, regardless of the method, than is really needed to achieve the desired therapeutic effect on, for example, a specific organ system or organ based receptor target fed by arterial blood. However, by introducing a drug substance into the arterial blood stream at its source, the lungs, a bolus of drug delivered to the target is less diluted, and, therefore, less drug needs to be deposited in-vivo at the site or entry point of administration (the alveoli).

Delivery of drugs via the lungs is the optimal approach to treat diseases in the lung. In addition, drugs delivered via the lungs for other than respiratory diseases, go rapidly and directly into the arterial blood, then to the heart, and then to the other critical organs such as brain, liver and kidneys, and receptor sites residing thereon. This reduces the effect of dilution on the administered therapeutic dose in the bloodstream. Furthermore, there is minimal enzymatic or acid activity in the lungs compared to the stomach that can impact the therapeutic molecular integrity of sensitive drug molecules such as genetically engineered peptides and proteins. Pulmonary drug delivery can, depending on the drug and disease:

a) improve the efficacy of a drug;
b) improve the bioavailability of a drug, which is particularly important for biological compounds such as peptides and proteins;
c) improve targeting to an organ or receptor site thus reducing unwanted side effects (which is an important consideration with, for example, anticancer agents); and
d) mimic the biopattern of a disease, or circadian rhythm, e.g., as in the case of sustained-release anti-hypertensives designed to peak coinciding with the early morning blood pressure surge.

Commercially, a new method of pulmonary drug delivery for an existing drug, can extend its therapeutic indications, lower cost, and facilitate a more rapid time to market. Since drugs administered by the pulmonary route do not require sterility, a sterile device or sterile environment, they are ideal for the delivery of drugs in difficult environments.

U.S. Pat. No. 6,125,844 discloses an apparatus for portable gas-assisted dispensing of medication not using a fluorocarbon propellant. The apparatus comprises a pressurized supply of gas containing therapeutic gas or mixture of therapeutic gases, and one or more drugs mixed therein, connected to a pressure regulator, wherein the pressure regulator is connected to a gas release switch which is connected to a breath activator. The breath activator is connected to an aspiration chamber, whereby in use when a patient inhales from the aspiration chamber, the inhalation causes the breath activator to engage with the gas release switch to release the therapeutic gas/drug mixture into the aspiration chamber, wherein the therapeutic gas and drug in the aspiration chamber are simultaneously delivered to a patient during inhalation. Alternatively, medication can be stored in a separate drug reservoir adjacent the pressurized supply of therapeutic gas, which medication is drawn into the aspiration chamber by a venturi assembly.

Variables that affect inhaler generated particulate drugs being delivered to the right location routinely mentioned in the medical literature include:

a) those that are breathing related including the volume of inspiration, inspiration flow rate (velocity), breath holding period after inspiration of a dose, the total lung volume at the time the bolus of medication is administered, and the expiration flow rate;

b) those that are particulate related including aerosol particle size, shape, density of the liquid or powder drug particles, and size distribution in the dry powder or liquid aerosol cloud produced; and c) the medical status of the patient, and in particular, the status of the respiratory system of the patient.

The objective with any method and technology involving inhalers, is: a) to generate particles of the optimum size range for deep lung delivery, and b) to get any administered particles past the larger airways where they will be lost to turbulence and impaction and into the middle (for treating respiratory diseases) and deep (for delivering drugs to the target area where they can enter the arterial blood) lung.

Unlike intravenously administered drugs, drugs administered via the lungs are not subject to prior first pass hepatic metabolism. They are also less subject to reacting with or being affected by fewer receptors prior to reaching their intended target either in the lungs or systemically, resulting in a reduced amount of drug being needed, if the particle size and delivery to the target location in the lungs are optimized. However, because any systemic drug administered by the lung does go straight to the heart first, the cardiac side effects of excipients and drugs administered by this method are an issue. As an example of the rapid effects drugs administered via the lungs can have systemically, administration of the pain killer morphine via the lungs is faster acting than morphine administered intravenously.

Recognition of the ability to deliver systemic therapeutic drugs by inhalation due to the physiological properties of the lung and circulatory system, has led to a large number of different therapeutic drugs being developed and evaluated for administration by inhalation to treat even non-respiratory diseases.

A key problem is in the maximizing the number of these smallest particles that are delivered to the terminal branches of the bronchioles and the alveoli. Small particles, preferably 1 µm-3 µm in size, are optimal for this purpose. Generally, only about 10-20% of the amount of particulate drug dispensed by conventional inhalers is delivered in this range.

Large molecule drugs, such as peptides and proteins which are now possible due to genetic engineering, do not pass easily through the airway surface because it is lined with a ciliated mucus-covered cell layer of some depth, making it highly impermeable. The alveoli however, have a thin single cellular layer enabling absorption into the bloodstream. The alveoli are the door to the arterial blood and are at the base of the lungs.

So, to reach the alveoli, a particulate drug must be administered in small size particles, and the inhalation must be moderated, slow, and deep. Large particles will impact in the oropharyngeal area or settle in the upper bronchi. If the particles are too small and/or ultra light, they will be exhaled (the latter is especially true if air is the tidal front of gas entraining the ultra light particles).

The larger passages through which the air and drug particles travel generates turbulence, which also results in the impaction and loss of drug particles. A desired goal is to increase the laminar flow of the gas stream in the larger air passages, so that particles reach the smaller passages where laminar flow is naturally induced. If there are any constrictions in the bronchi or bronchioles, resulting, for example, from asthma, the turbulence and rate of impaction of drug particles can also increase at those points of constriction.

Any variability in the dose deposited in the lungs, and where it is deposited in the lungs, could have a major effect on treatment because of the narrow therapeutic range of many drugs, and the potency of such drugs. One well known such example is insulin.

Aerosol particles are deposited in the airways by gravitational sedimentation, inertial impaction, and diffusion. All three mechanisms act simultaneously. However, the first two are the principle methods that apply to the deposition of large particles. Diffusion, is the primary factor of deposition of smaller particles in peripheral regions of the lung.

The optimum size particles of drug for delivery to the alveoli are in the range generally of 1-3 microns, and usually particles less than 2 microns reach the alveoli.

The diameter of therapeutically usable particles is generally between 0.5 and 5 microns. Particles 1-5 microns are deposited in the larger airways while particles generally below 3 microns in diameter reach the terminal bronchioles and alveoli and are optimal for transference into the arterial blood. The depth of penetration of a particle into the bronchial tree is inversely proportional to the size of the particle, down to 1 μm. Particles smaller than 1 μm, however, are so light that a large proportion does not deposit in the lungs.

The small airways are the optimal sites for the inhalative treatment of obstructive pulmonary diseases. Diffusion is a process that applies to particles smaller than about 3 microns. The maximum collection of particles by the deep lung is by the process of sedimentation.

Some of the sub-micron particles of a drug may be exhaled because their sedimentation may not be high enough in air— which is normally the ambient entrainment gas and environment in the lungs.

Prior art, whether metered dose inhalers (MDI) or dry powder inhalers (DPI), use air as the exclusive or primary means of conveying fluidized powder or aerosolized liquid drug into the lungs. In the case of MDIs, it is assumed that the propellant evaporates as intended or constitutes a very small fraction of the total gas inhaled at full tidal volume with the drug dose and air.

Heliox has been administered to a patient in a hospital setting prior to the administration of a dry powder or liquid aerosol drug. Heliox has also been used to administer a liquid drug using a nebulizer, which is a different type of device for pulmonary drug administration lasting 10-60 minutes. That is distinct from "puffs" received through an inhaler. Additionally, in both cases, the systems in which Heliox were used were designed for the physical properties of air and not Heliox, and so were not optimized for Heliox.

Prior art and medical publications pertaining to inhalers, address other factors but do not focus on the specific gas involved in the transport of particles into the lung. In the case of DPIs, the gas is always assumed to be, or stated specifically to be, air. In the case of MDIs, the "gas" is always assumed to be a liquid propellant having a vapor pressure, CFC in most cases, and is only a negligible fraction of the inhaled volume, the balance being air.

MDI is a metered dose inhaler consisting of a propellant generating a vapor pressure and a drug in suspension or solution form, where, when the device is activated, the vapor pressure of said propellant pushes a predetermined amount of liquid drug through a nozzle generating an aerosol for inhalation. MDIs contain suspensions or solutions of a drug, a propellant, and a surfactant that acts as a lubricant to stop particles from aggregating and to reduce clogging of the aerosol nozzle. MDIs rely on the use of propellants that have a high vapor pressure. The higher the vapor pressure, the faster a liquid containing a drug can be pushed out of a nozzle, and thus a thinner liquid sheet is formed, and smaller particles are produced. Vapor pressure is therefore directly related to the velocity generated and the fraction of fine or desirable small particles generated.

Pressurized aerosols historically used chlorofluorocarbon (or CFC) propellants generating a pressure of approximately 400 kPa or higher. The aerosol cloud therefore emerges from the canister at a high speed. Furthermore, the drug crystals are initially enclosed within large propellant droplets whose mass median diameter may exceed 30 μm. Large particles traveling at high velocities are very susceptible to oropharyngeal deposition by inertial impaction. While the propellant evaporates and the particles slow down when the device is held away from the mouth, or when an MDI spacer is used, on average, only about 20% of the original or nominal dose actually enters the lungs.

In an MDI, the generation of an aerosol occurs in what can only be described as an explosive manner since the propellant containing the therapeutic solution or suspension disintegrates as it passes through the aerosol nozzle at very high velocity. As the propellant flash rapidly evaporates, the liquid particles decrease rapidly in diameter to the state of a "dried solute".

The velocity of the discharged particles entrains the evaporating particles as they exit the device and move into the airstream. This velocity is much higher than an inhalation velocity by a user. The result can be impaction of particles in the oropharyngeal area. A spacer, which is discussed later, is a solution to this problem, i.e., reducing the velocity of the "cloud" of particles prior to inhalation. Another technique is to use the "open-mouth" method that implies activating the device a few cms away from an open mouth.

MDIs containing a suspension require that they be shaken before use. MDIs containing a solution need not be. This presents a problem to patients using more than one type of drug, i.e., one in suspension and one in solution, as the patient may shake the wrong MDI, or not shake the MDI that needs to be shaken before use. The latter one would result in an incorrect dose of the drug being delivered and inhaled. This is an advantage to the use of DPIs, as there is no "to shake or not to shake" decision. MDIs containing propellant and a suspension or solution, also present a challenge concerning stability over a temperature range.

A problem with both MDIs and DPIs is that there is often poor coordination between the patient pressing the actuator and the timing of the inhalation. One solution is to use a spacer between the device and patient, that will also allow for the heavier particles to settle before the patient inhales.

Another problem with MDIs is that they are based on propellants that rely on vaporization to generate pressure, and a drop in temperature occurs when vaporization occurs. The vaporized propellant can hit the back of a user's throat before it has completely evaporated if no spacer is used. This can lead to reflex gagging which interrupts the continuous and deep inhalation required for optimum delivery of the drug. In addition, water moisture in the mouth will condense rapidly in the cold vapor, causing the small liquid medication droplets to coagulate and drop out, reducing the percentage of drug actually deliverable past the oropharyngeal area.

DPI is a dry powder inhaler consisting of a drug in micronized dry powder form provided in a compact shape and contained in a unit dose container or reservoir, which is fluidized by the flow of a gas and inhaled by the patient.

Micronized dry powder formulations are very soluble and quickly dissolve in the fluid layer on the surface of the deep lung before passing through the thin single cellular layer of the alveoli. They are then deposited in the alveolar region and can be absorbed into the bloodstream without using what are commonly referred to as penetration enhancers. Dry powder aerosols can carry approximately five times more drug in a single breath than metered dose inhaler (MDI) systems and many more times than liquid or nebulizer systems.

Micronized dry powder drugs used in inhalers are usually produced with an original particle range of 1-10 microns. An individual dose as loaded can take from 5 mg to 20 mg of dry powder drug. A lower total amount of dry powdered drug is possible with purer drugs, or with drugs that do not require or are packageable without excipients. Examples of excipient carriers used in dry powder drug formulations include lactose, trehalose, or crystalline or non-crystalline mannitol. Trehalose and mannitol, which are spray dried sugars, are better dispersal agents than lactose.

Thus, the "drug substance" in a DPI consists of the pure drug, plus a sugar if an excipient is used, compared to the multitude of constituents contained in a MDI. This multitude of constituents in a MDI increases the work involved in production of the product and its packaging, can effect formulation stability, can cause aerosolization problems by clogging the nozzle, and may require either the shaking or non-shaking of the MDI Inhaler before use.

In DPI devices, providing compressed gas or propeller/impeller assisted fluidization, basing the fluidization on the patient's inhalation produces a major variability in dosing and particle size formation. The velocity, ramp up rate, and continuous event of this inhalation are variables that can effect the fluidization of the powdered drug and the effective delivery of the optimum size particles to the deep lung. The higher the rate of gas velocity, the finer the particle size created during fluidization, but the greater the possibility for impaction of particles in the oropharyngeal area during inhalation, where the gas velocity which fluidizes the dry powder drug is derived from the "suction" or negative pressure of a strong inhalation.

Devices that rely on the force of the patients inhalation, also operate based on the "suction" or pulling effect of said gas flow, i.e. a negative pressure, to pull apart and fluidize the drug powder. This is less effective than a highly focused directed stream of high pressure gas, which is consistently delivered at the same pressure.

Some DPIs use compressed air generated by a pumping mechanism, which the patient utilizes, whereby the pressure is released for fluidization of the powder drug when the system is actuated. The pressure, and therefore velocity, of a gas that can be generated by a hand pump or an inhaler device, is far less than that available from a compressed gas cartridge. The uniformity of fluidization of the dry powder would therefore be less using a manual hand pump, with the possibility therefore of generating larger percentages of larger size particles, which result in the variable and inconsistent loss of drug in the oropharyngeal and upper bronchi.

The higher the velocity of the gas hitting the dry powder, the greater the amount of powder dislodged and the turbulence induced, which can create a cloud of particles for inhalation. In the case of dry powder inhalers, the ramp speed to the velocity required to deaggregate or deagglomerate the dry powder into fine particles, is as important a factor as velocity in determining effectiveness.

Systems using dry powder drug in capsules, require the patient to load the capsules individually, whether the system is capable of being loaded with one dose at a time, or several doses for multi dose use over time. In some of these devices, the capsule is crushed to thereby release the powder contained therein.

A DPI entrains the fluidized drug powder and sends it through a narrow gap, increasing the velocity of the gas and powder to improve deagglomeration by turbulence and reduce the number of large particles by impaction or settling out. Often, a baffle is also included in the system to trap larger particles.

One problem in using compressed gas vs. a hand pump to generate compressed air DPI (or a liquid MDI driven by CFC vapor pressure) is that the compressed gas pressure will decrease with usage. In the case of the hand pump driven DPI, the gas pressure is consistent during each dose fluidization procedure. In the case of gas driven MDIs, the pressure available for aerosolization decreases over time near the end of the capacity, unless the MDI has a cut off which does not allow dose administration below a certain minimal pressure required to achieve sufficient aerosolization.

A spacer is a plastic or metal tubelike device that is placed between the inhaler device and the patient, and into which the inhaler device delivers the particulate cloud generated by dry powder fluidization or liquid aerosolization. A spacer can be open-ended, allowing a slowing down of the gas, or closed-ended (holding chamber) to reduce the loss of dose inhaled due to poor hand-breath coordination. The spacer slows down the gas mass and particles leaving the inhaler, traps larger particles by impaction and settling, and provides a better control of inhalation rate and timing, delivery of the desired size range of particles, and reduced oropharyngeal loss of particles due to impaction, versus inhaling directly from the inhaler device. It also reduces the gagging effect from inhaling a cold gas like Freon. Spacers have been incorporated into the routine use of MDIs.

Inhalation flow velocity in inhalation driven inhaler determines the quality of the aerosol cloud, as the greater velocity fluidizing the dry powder drug, the finer the particles produced. However, the inhalation of particles at a fast rate, leads to impaction of a large percentage of particles on the back of the throat.

Heliox, which is commercially available in a combination of 70% or 80% helium in oxygen, has been used for over 70 years in respiratory therapy. Heliox is administered in some hospitals and emergency rooms in large gas cylinders. The most popular types are the "K" cylinder that stands 51 inches in height, 9 inches in diameter and weighs 130 lb when fully filled. Heliox is supplied at 2,200 psig and requires a two-stage pressure regulator to reduce the pressure for administering to patients. However, due to its bulkiness and requirement of sophisticated pressure and flow regulators, it is used only in research and hospital facilities.

Gas flow within the tracheobronchial tree is complex and depends on many factors. For a given pressure gradient, the volumetric flow rate of a gas is inversely proportional to the square root of its density. In accordance with the subject invention, it has been found that substituting helium for nitrogen in inhaled gas mixtures results in increased gas flow rates because the density of helium is much lower than that of nitrogen.

Resistance to the flow of gas within the tracheobronchial tree results from convective acceleration and friction. Convective acceleration is the increase in the linear velocity of fluid molecules in a system of flow in which the cross-sectional area is decreasing. Frictional resistance may be either turbulent or laminar depending on the nature of the flow. Since resistance associated with these factors is density-dependent, breathing a less dense gas should decrease flow resistance and, consequently, reduce respiratory work. An obstruction in the upper airway causes a resistance to flow that is primarily convective and turbulent and therefore susceptible to modulation through a change in gas density. For respiratory treatment, it is desirable to create a flow of minimum pressure drop or flow-resistance.

Gas flow in airways may be laminar, turbulent, or a combination of the two. Turbulence is predicted by a high Reynolds number, which is a unitless quantity proportional to the product of gas velocity, airway diameter, and gas density divided by viscosity. The Reynolds number is also expressed as the ratio of kinetic to viscous forces. The decreased density of helium, when substituted for nitrogen, lowers the Reynolds number and may convert turbulent flow to laminar in various parts of the airway. Turbulence is highly dependent on the surface roughness, so that a flow in a rough cavity might be turbulent even if the Reynolds number predicts a laminar flow. Even in the absence of turbulent flow, the decreased density of helium improves flow and decreases work of breathing along broncho-constricted airways.

The efficacy of Heliox in respiratory therapy occurs because it is a low-density gas. The rate of diffusion of a gas through a narrow orifice is inversely proportional to the square root of its density (Graham's Law). When an area of stenosis occurs in the airway, there is resistance to flow at the site of the stenosis. The resistance varies directly with gas density. Downstream from the stenosis, airflow becomes turbulent. By substituting helium for nitrogen in inspired air, resistance at stenotic areas is reduced and turbulence downstream from the stenosis is either reduced or eliminated.

In the tracheobronchial tree, a laminar flow normally exists in airways that are generally less than 2 mm in diameter. Turbulent flow has been observed in the upper respiratory tract, the glottis, and the central airways. This upper portion of the airway, especially the throat, and the main bronchioles, are considered to be the region where the turbulent intensity is sensitive to the gas density.

Since airway resistance in turbulent flow is directly related to the density of the gas, Heliox, with its lower density than nitrogen or oxygen, results in lower airway resistance. Heliox further lowers airway resistance by reducing the Reynolds number, such that some areas of turbulent flow are converted to laminar flow. The higher flow rate of Heliox has the ability to stay laminar at velocities under which air would be turbulent.

Heliox does not need to be laminar to provide higher flow rates and its benefits persist under turbulent conditions. Some have the misconception that, due to its lower density, helium is less viscous than air, so it flows faster. Actually, the absolute viscosity of helium is slightly higher than that of air, and its kinematic viscosity (absolute viscosity divided by density) is about seven times that of air. Thus, from the fluid-dynamical standpoint, helium is more viscous than air.

The linear relationship between helium concentration and resistance to flow is predictable on the basis of fluid mechanics. Helium has two major effects in reducing resistance in an obstructed airway. First, helium reduces the probability of turbulence. Flow of air in the upper airway is turbulent, except at rest, because of the rough walls of the airway and the relatively short lengths of the airway segments compared to their diameters.

The probability of turbulent flow is predicted by the Reynolds number:

$$Re = \frac{\rho V D}{\mu} \qquad (1)$$

Where
  D=Diameter of the mouth, airway or throat (cm)
  V=Gas velocity (cm/sec)
  $\rho$=Density of the gas (g/cc)=
  $\mu$=Viscosity (g/cm/sec)

Second, gas flow through an orifice requires an increase in pressure to maintain the flow:

$$U_o = \frac{C_o}{\sqrt{1-\beta^4}} \sqrt{\frac{2(P_a - P_b)}{\rho}} \qquad (2)$$

where $P_a - P_b$ is the pressure difference caused by the orifice (dynes/cm$^2$), and $C_o$, is the discharge coefficient, which depends on the sharpness of the edge of the orifice.
  $U_0$=Velocity through the orifice
  $\beta$=Ratio of orifice diameter to pipe diameter
  $P_a$=Pressure at upstream before orifice
  $P_b$=Pressure at downstream after orifice.
  $\rho$=Density In summary, Heliox is more beneficial because of its lower density. Compared to air, it flows at a higher flow rate for fixed pressure gradient, or needs a lower pressure gradient or work of breathing (or patient inhalation effort) for a given flow rate. This is valid even in turbulent conditions.

There is medical literature where Heliox has been provided to a patient prior to dosing with an Inhaler based on a CFC based propellant. There is also a study where a small volume of Heliox (40-70 ml) was delivered as bolus but with a shallow breath during pulmonary administration of a particulate to see if the entrained particles would diffuse deeper into the lungs by themselves within the Heliox gas.

There is also literature where Heliox was used with a nebulizer to deliver a drug in liquid form. Most of the time, the velocity of the nebulizer gas flow was based on that used for air. In other cases where the gas flow velocity was altered, the aerosol nozzle used was designed for air and not Heliox or pure helium, so that the particle size distribution was not adapted to the change of gas.

Two factors that can influence the delivery of an optimally fluidized dry powder drug formulation are static electricity and humidity. It is desirable to avoid imparting a static electricity charge to the fine particles, especially those 1 micron or less in size. The static charge will form an attractive force on the particles, causing them to clump together, rendering them of a collective size that is unsuitable for deep lung delivery. This type of particle cohesion is highly undesirable because a few particles that are attracted together can double or triple the terminal settling velocity. This is a key reason why conventional inhalers using inhaled air, propeller driven air, or compressed air pumps, have more than 50% of the drug lost in the mouth and throat, before they can enter the lung.

Moisture in the fluidization gas can also result in the clumping of particles. This is a disadvantage of using inhaled air, air from the surrounding environment driven through a propeller, or air compressed using a hand pump that is part of an inhaler. If an inhaler is used in a humid geographical location or during humid seasonal conditions, the humidity can affect the deliverable dose of drug particles in the size range required for penetration into the deep lung, thereby affecting the dose.

In addition, if moisture comes in contact with the powder before it is fluidized, the moisture can accumulate on the outer layer of the powder, forming lumps before fluidization occurs.

The subject invention system can be light enough to be portable, and small enough for a child up to an adult to hold and use.

It is an object of the subject invention to provide an inhaler that can deliver appropriate sized particles to the lungs efficiently using a propellant with sufficient pressure to fluidize or aerosolize a drug to be used by a patient.

SUMMARY OF THE INVENTION

The present invention describes in detail an inhaler for medical purposes where the main carrier gas is Heliox or helium. One embodiment of the invention is an inhaler for introducing a drug into a user, said inhaler comprising:
- a first chamber adapted for containing first a compressed gas at a first pressure;
- a second chamber in selective communication with said first chamber, said second chamber adapted for containing a second compressed gas at a second pressure lower than the first pressure, said first and second chambers cooperating so as to yield said second pressure of said compressed gas within said second chamber;
- a means to administer two different volumes of gas in successive applications from the second chamber;
- a storage section coupled to said second chamber, said storage section adapted for containing a drug and operating such that a portion of said second compressed gas can fluidize and aerosolize said drug to thereby produce a drug cloud; and
- a mouthpiece coupled to said storage section, said mouthpiece adapted for receiving said drug cloud and convey said drug cloud to a user.

The inhaler is comprised of three mostly independent parts: a high-pressure canister, a drug delivery holder, and a spacer. The three parts can be separable from each other or affixed in a non-separable way. The canister can have a resealable, refilling opening and the drug holder can be removable and have a resealable refilling means. The high pressure canister holds pressurized Heliox or helium and delivers two constant volumes of gas at a fixed pressure independently of the inside pressure of the canister. One volume of gas can go directly to the spacer to purge it from ambient air, while the second, smaller, volume of gas will interact with the drug. The drug drum holds several doses of drug in liquid or powder form that will be nebulized or liquefied using the second volume of gas from the canister. Finally a spacer is used to hold and mix the two volumes of gas from the canister and opens up to the patient. Alternatively, only one volume of gas can be released by the canister to purge and nebulize the drug in one process.

These aspects, as well as others, will become apparent upon reading the following disclosure and corresponding drawings. The drawings will cover only some embodiments of the invention to explain its overall functionality. There is wide room for design changes on the technical aspect of the gas delivery for instance. No figure is drawn to scale.

In order to position a helium/Heliox canister on the market, it is necessary to produce a product of similar weight and dimensions as current MDIs. The weight when full is estimated at 50 grams. Helium itself is a light gas and will contribute only slightly to the overall mass of the canister. Indeed, 300 ml of pure helium weights 50 mg, so 100 doses of 300 ml would only weight 5 grams.

It is hence preferable to minimize the weight of the canister. Its sizing, however, depends on the inside pressure of the gas, but pressure will limit the total amount of gas in the device, or the total number of doses available. We will base our calculations on average canister dimensions of 80 mm height by 40 mm diameter, containing roughly 100 cc of gas. Assuming 10 doses, or 3 liters of gas, the canister will need to be pressurized at 500 psig. The device would then weight 50 grams using steel (stainless or carbon). If we want to deliver 50 doses (comparable to existing MDIs), the canister should then be pressurized at 3,200 psig and will weight 320 g (steel). See Table 2 for details.

TABLE 2

Design of proposed canister.
Height 80 mm, diameter 40 mm
(dimensions based on existing MDIs).

|  | Number of doses | | |
| --- | --- | --- | --- |
|  | 1 | 10 | 50 |
| Inside pressure (psig) | 50 | 500 | 3,200 |
| Volume of gas (liters) | 0.34 | 3.3 | 15 |
| Thickness (mm) | 0.05 | 0.5 | 3.2[a] |
| Weight Full (grams) | 5 | 50 | 320 |

[a]The overall dimensions of the canister are changed due to the high thickness.

An optimization of the dimensions of the canister can be easily done so to have an acceptable overall weight, inside pressure and number of doses available. For instance a 25 cc container at 1,600 psig can also deliver 10 doses, while weighting 30 g.

A helium canister can not compare to existing MDIs as described herein. For a similar number of doses, it will be too heavy and pressurized at dangerous levels. This is due to the fact that the canister needs a much higher amount of gas per dose to fully use helium properties.

The solution is to design the canister for a very limited number of uses. Synchronizing the number of available doses in the canister with the number of drug packages in the drum (plus a residual volume necessary to delivering the gas) ensures that patients will never operate their devices without the necessary drug. A cylinder containing the necessary amount of helium/Heliox for 10 doses would weight roughly 40 grams full (37 grams material, less than 1 gram for the gas), which is comparable to existing devices. Finally it would market itself along with existing DPIs in terms of number of available doses, but with a much better efficiency due to the use of Heliox/helium for better drug delivery and the absence of patient hand-breathing synchronization.

In order to help leverage the cost of the inhaler over longer period of uses, the canister can be refillable. In this case, the user would also have a bigger, high-pressurized helium/Heliox cylinder at home and would refill his small inhaler canister with a simple process after a certain number, 10 for instance, of uses. This idea is novel to inhalers and would allow the patient to use their inhalers for months at a time without a refill from health care providers. In this case, the drug drum could be allowed to contain a much higher number of doses. Refilling the cartridge could be done with no or very little modification to the current proposed cartridge and gas delivery designs.

The canister's maximum pressure is 500 psig. An E-cylinder is typically filled up to 2,200 psig for a total content of 623 liters for 100% helium or 708 liters for pure oxygen. Using an E-cylinder to refill the canister with a basic regulator set up for a delivery of 500 psig would allow refilling the canister with 1,600 doses or 480 liters based on the content for the helium E-cylinder.

Practically, the in-home Heliox tank would have a standard regulator set up for a delivery of 500 psig. The easiest way to refill the canister is to have a separate valve on the canister for refilling purposes only. The valve could be similar to a standard one-way refilling valve as used on footballs for instance and located on top or on the side of the canister to avoid any interference with the metering chamber inside the canister. For aesthetic and safety reasons, it is preferable that no extension protrudes from the cylinder. The valve would only open if the proper stem from the in-home refilling tank is inserted and, due to the regulator of the home cylinder, would refill the portable cylinder to exactly 500 psig, or 10 doses. The operation would only require the user to push the cylinder on the valve stem and would last a few seconds. A pressure gage on the home cylinder would let the user know when the inside pressure falls below 500 psig, the pressure when the cylinder would be considered having reached the end of its usable life. Alternatively a counter device would let the user know how many refills are available in the home cylinder.

The whole refilling system would only require the regulator on top of a standard medical cylinder along with the specific valve stem and the pressure gage or dose counter. This clearly limits the overall cost of the device. Renting the home cylinder to the user would further reduce the costs by reusing the device and refilling it in specialized facilities in a similar fashion to existing Oxygen cylinders.

DETAILED DESCRIPTION OF THE PREFERRED EMBODIMENT(S)

Figure 1:
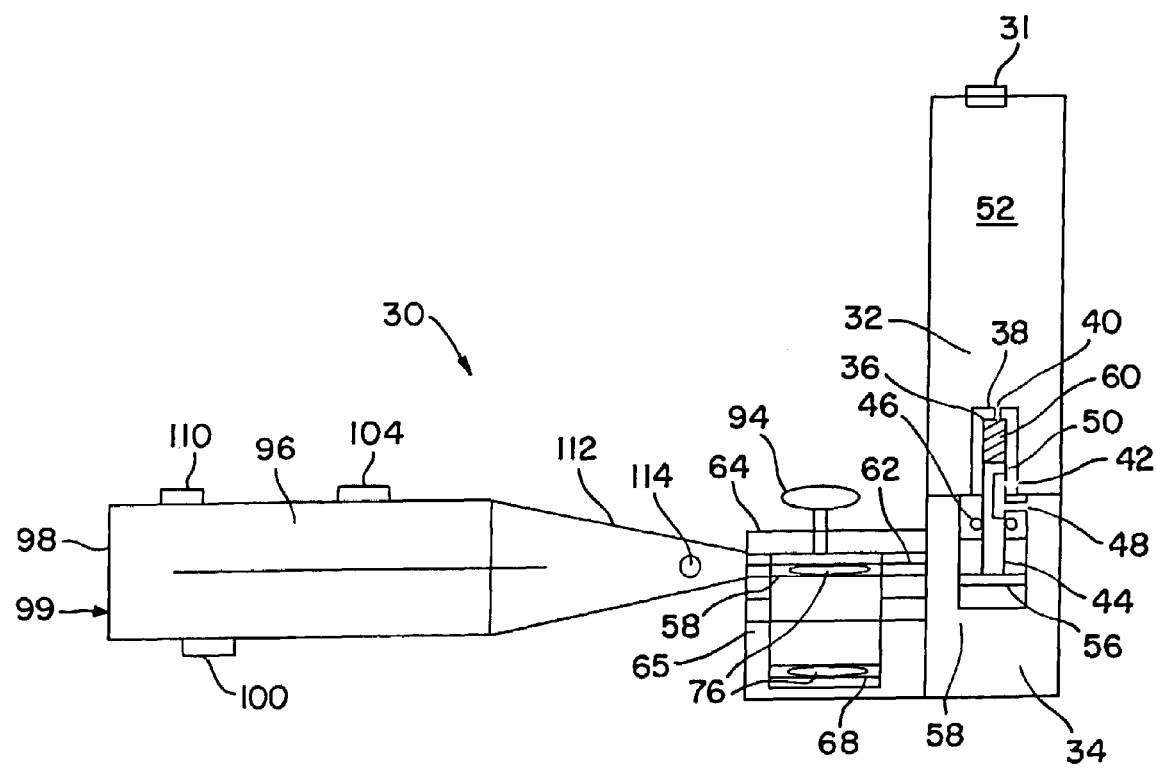
FIG. 1 is a side view of an inhaler, diffuser, and spacer in accordance with the invention.

Referring to FIG. 1, there is shown an inhaler 30 in accordance with the invention. Inhaler 30 comprises a high pressure chamber 32 coupled to an equalization chamber 34. High pressure chamber 32 is a small, cold rolled, low carbon steel container containing gas 52 compressed to a pressure between about 30 psig and about 1600 psig, preferably between 100 psig and about 500 psig. Gas 52 is a gas preferably containing from 0% to 100% of helium, the balance if needed being oxygen. Other compressed gases could also be used. It is preferred that the gas that is used be a dry gas. The high pressure storage allows Heliox to be stored in a container preferably 10 cc to 100 cc in volume but still provide sufficient gas for a large number of inhalations. For example, 100 cc of Heliox at 200 atmosphere will expend 200 times in volume to a volume of 20 liters when the gas is released to atmospheric pressure.

To provide Heliox at a constant pressure, the storage pressure in chamber 32 should be significantly higher than the regulating pressure. When the supply pressure of the compressed Heliox falls below the pressure required to fluidize the powder (or aerosolize a liquid) to the uniform standard established, then the inhaler should become inoperative, and a cut off mechanism is thus desirable. The chamber could have a resealable, refilling opening 31 to which a user can couple the canister to a larger high-pressurized Heliox tank.

High pressure chamber 32 includes a housing 36 defining a third chamber 38. Housing 36 includes an opening 40 on a top portion thereof and a gas passage 42 on a side. Third chamber 38 communicates with both high pressure chamber 32 and equalization chamber 34. Equalization chamber 34 is needed to produce a consistent volume of gas throughout the lifecycle of the high-pressure canister 32 independent of its inside pressure. This is achieved with the help of a simple regulator via the diaphragm plate 56. Gas will flow from the high chamber 32 to the equalization chamber 34 until equalization chamber 34 has reached its nominal pressure, constant value much smaller than the high-pressure at which the gas is stored in the canister 32.

Equalization chamber 34 includes a housing 58 having a gasket 46 disposed therein. Gasket 46 includes a gas passage 48 on a side thereof for allowing gas disposed in third chamber 38 to communicate with second chamber 34.

A piston 44 is slidably mounted within gasket 46 and within housing 36. Piston 44 includes a communication opening 50. Piston 44 is pushed downwards with a spring 60 located inside chamber 38 to allow gas communication between chambers 32 and 34. When the canister 32 is separated from the inhaler, the spring 60 is pushing the piston 44 sealing the canister by closing the opening 42. When the canister is inserted in the inhaler, the tip of the piston 44 will rest on the diaphragm 56, and pushing the piston 44 up inside chamber 38 just so that high-pressure gas passage 42 is communicating with the communication opening 50. Communication opening 50 is designed to selectively allow gas 52 stored in high pressure chamber 32 to communicate with gas 54 stored in equalization chamber 34. A pressure plate 56 is also disposed within housing 58. One side of pressure plate 56 is coupled to piston 44.

Through the use of high pressure chamber 32 and equalization chamber 34, inhaler 30 produces a desired gas pressure without requiring an external pump or inhalation pressure from a patient. When the pressure inside the equalization chamber 34 is too low to allow inhaler 30 to be used, it is desirable that the high-pressure Heliox 52 from high pressure chamber 32 will fill into equalization chamber 34. Spring 60 and pressure plate 56 are designed so as to facilitate this operation. As stated above, piston 44 has a communication opening 50 that selectively allows high pressure chamber 32 to communicate with equalization chamber 34 through gas passages 42 and 48 when passages 42, 48 are aligned with communication opening 50.

Gas 52 applies pressure against a small area defined by the top of piston 44. The net force from gas 52 pressing on piston 44 is the pressure of the gas multiplied by the surface area of the top of piston 44. This net force applied by the high-pressure side of high pressure chamber 32 on piston 44 works with the biasing force of spring 60 and against the force applied by gas 54 on pressure plate 56.

The spring constant of spring 60 and the surface area of pressure plate 56 are chosen so that when equalization chamber 34 has received sufficient pressure to utilize inhaler 30, the force applied by gas 54 on pressure plate 56 will exceed that of the force produced by gas 52 on piston 44 on the high-pressure side of the device and the force of the spring 60. At such a time, the force applied by gas 54 will cause piston 44 to move upward within housings 58 and 36. As piston 44 moves upwardly, communication opening 50 will move away from gas passage 48 effectively stopping any additional high-pressure Heliox 52 from entering equalization chamber 34. The spring 60 will push the piston 44 downwards to allow gas passage from chamber 32 to chamber 34 no matter what the pressure is inside chamber 32. Since the surface of the pressure plate 56 is quite important, the two main forces balancing the piston are the spring force and the pressure force from the equalization chamber 34. The spring constant of spring 60 and the area of pressure plate 56 are thus selected for a specific pressure rating so that a patient will always receive the same volume of gas and dosage for their applications, independent of the pressure change in high-pressure chamber 32.

Once gas 54 is dispensed (i.e., inhaler 30 has been actuated and the medication in inhaler 30 is delivered to the patient), the pressure exerted by gas 54 on pressure plate 56 is lower and the high-pressure Heliox 52 along with the spring 60 will force piston 44 downwardly thereby repeating the cycle described above until equalization chamber 34 once again has a desired pressure of gas therein.

An alternative to this delivery system can be done using a mechanical actuation by the user. As the high-pressure chamber 32 is depressed, the piston 44 will allow the gas to escape from the high-pressure gas passage 42 and be stored into a secondary chamber. The amount of gas released into equilibrium chamber 34 is then defined by the volume of this secondary chamber. The gas is released from this chamber into the equilibration chamber 34 when the high-pressure cylinder 32 is returned to its original position. In this configuration the housing 58 could be used as the secondary chamber.

The high-pressure Heliox 52 can be stored at, for example, 1,600 psig. Equalization chamber 34 effectively decompresses this gas so that it has a pressure of, for example, 32 to 200 psig. Using 22 ml of the 200 psig Heliox, the gas will expand to 300 ml at a pressure of one atmosphere. This is a sufficient amount of gas for drug delivery in one inhalation.

It should be noted that the equalization chamber 34 can be part of the separable high-pressure canister 32. In other words, the design of the delivery of a constant volume of gas can be an internal mechanism inherent to a high-pressure canister that the user can buy independently of the rest of the inhaler, or it can be part of the inhaler itself.

Equalization chamber 34 contains a fixed volume of pressurized gas 54. This gas will be released in two widely different volumes to the rest of the inhaler. The first volume released is around 270 ml of gas; the second is roughly $\frac{1}{10}^{th}$ that value, or 30 ml. It is proposed here that the creation of the two volumes occurs in separate activation, either triggered manually by the user (i.e. pressing a trigger twice or at two positions) or sequentially inside the device. The drawings will cover 2 different embodiments of the invention: mainly either delivering two volumes of gas using a two-chamber piston (FIG. 2), or with the use of two gas orifices, one being a calibrated orifice (FIG. 3).

Figure 2:
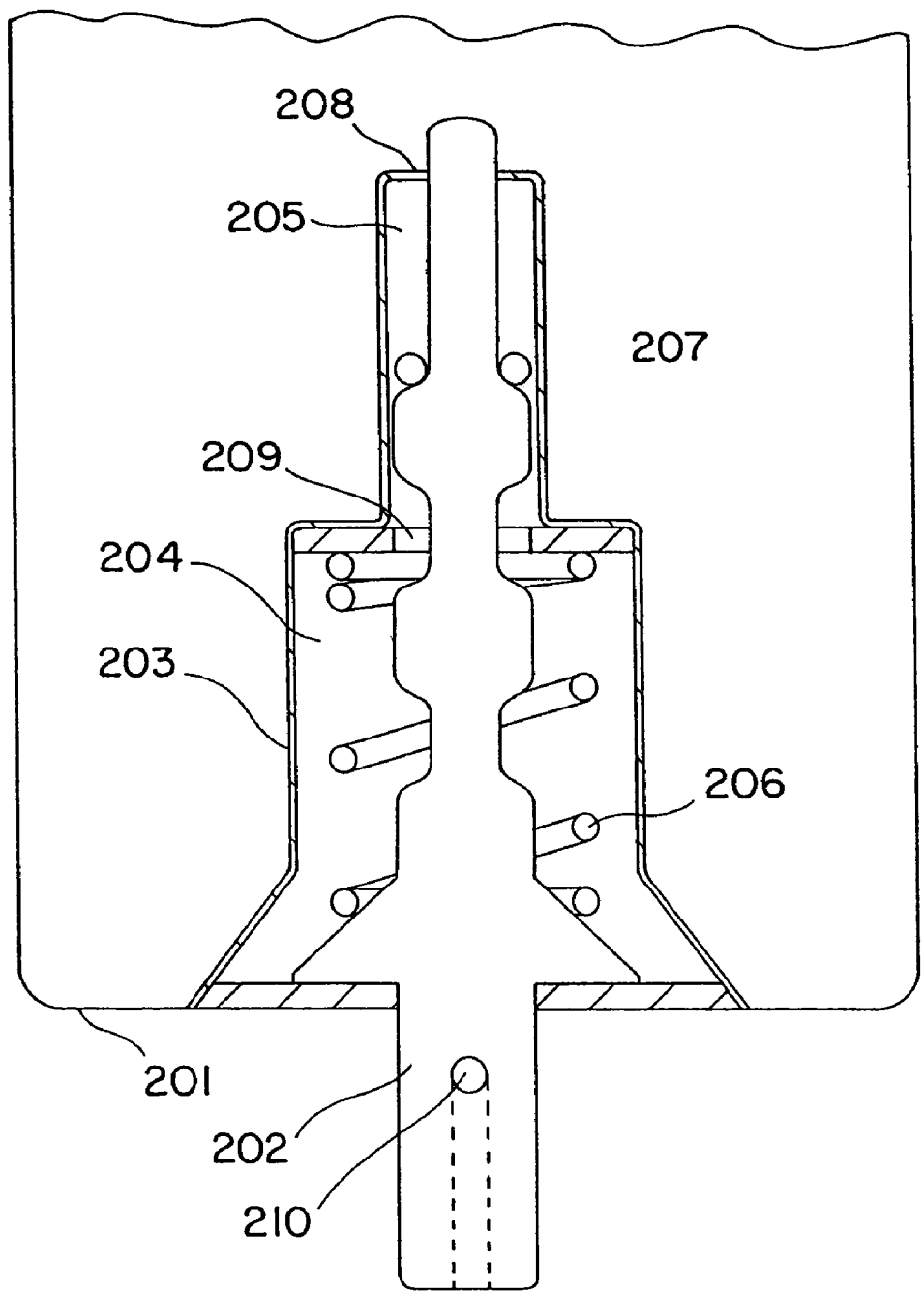
FIG. 2 side view of a piston-chamber assembly to deliver the two volumes of gas.
Figure 3:
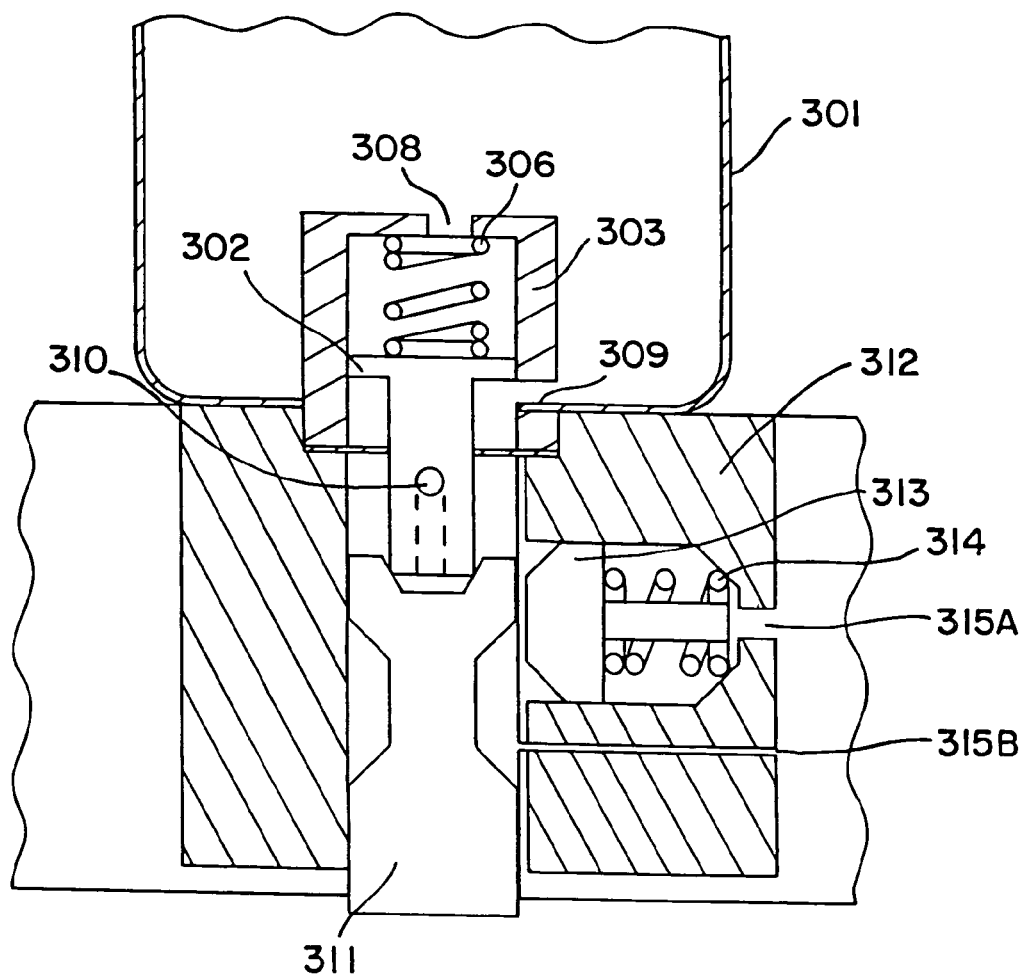
FIG. 3 is a an alternative to FIG. 2 to deliver the two volumes of gas using two gas orifices, one being a calibrated orifice.

Option 1:

The two-volume delivery can be done first by having two-chambers as seen in FIG. 2. The novelty aspect lies in the presence of two internal chambers and a unique piston shape, selectively isolating the chambers. Option 1 also allows for the delivery of the two-volumes of gas to be an inside component of the high-pressure canister 32. The two-volume delivery can be inherent to the canister design where the two chambers are an internal mechanism of the canister, along with the equalization chamber. It is for that reason that the valve assembly has been designed to closely resembles existing MDI canister design. If the two-volume delivery is thought of belonging to the inhaler instead, the piston shape can be changed to ease its manufacturing.

The shape of the piston is adapted to deliver first with a low push activation a high volume of gas (i.e. 270 ml) that can be used to purge the spacer. Using a higher push activation will deliver a much smaller volume of gas (i.e. 30 ml) to nebulize the drug. Releasing the stem valve allows the two chambers to communicate with the equalization chamber refilling them for the next use.

Equalization chamber 201 includes an internal housing 203 defining two different size chambers 204 and 205. Housing 203 includes an opening 208 on top for communication with the equalization chamber. First chamber 204 communicates with second chamber 205 via opening 209, and the outside via the opening 210 in the main piston 202. Second chamber 205 communicates with both equalization chamber 201 and the first chamber 204 via the openings 208 and 209 in housing 203.

A piston 202 is slidably mounted within the gasket 203. Piston 202 includes a communication opening 210 comprising of a hollow passage terminated at the bottom of the piston. The communication opening 210 is designed to selectively allow gas stored in chamber 204 to communicate with the outside of the canister. The unique shape of the piston 202 allows for the two-process operation.

At rest, piston 202 is pushed downwards by spring 206 located inside the housing 203, isolating the chambers with an isolation ring. Communication openings 208 and 209 are opened allowing filling of the second and third chamber 204 and 205 from the equalization chamber 201. When the user wants the delivery of the first volume of gas, piston 202 is sliding upward relative to the chamber 201. The opening 210 is now communicating with chamber 204, releasing the first initial large volume of gas. In this position, piston 202 pushes against the isolation ring surrounding opening 209, closing opening 209 and isolating chamber 204 from chamber 205. All the gas in chamber 204 will leave until equilibrium is reached with the outside of the canister.

To release the second volume of gas, the piston 202 is moved further up. Gas can now flow from chamber 204 to chamber 205 via opening 209, and to the outside via opening 210. The O-ring 207 affixed to the piston 202 will now isolate chamber 205 from the main high-pressure gas in the canister 201 by sealing opening 208. Since opening 208 is smaller in diameter than the piston, it will also limit the maximum upward movement of the piston 202 and the overall amount of gas delivered in one dose. Since chamber 205 is much smaller than chamber 204, it will deliver a smaller volume of gas to be used for the drug delivery.

Option 2:

The other option is to control the delivery of the two volumes using calibrated orifices. In this case, the design of the high-pressure canister is similar to existing ones, the novelty lying in the design of the inhaler main chamber.

The main process is located inside the inhaler, communicating with the equalization chamber 34 via a piston 302, as seen in FIG. 3. In this case, the canister 32 along with the equalization 34 can be a detachable item of the inhaler; it will now be referred in general term as the canister 301. The delivery of the two volumes is inherent of the inhaler body.

Piston 302 is pushed open by a user-activated valve 311. The valve 311 is encased inside a casket 312 which has two gas passages 315A and 315B connecting the high-pressure gas from the canister 301 to the rest of the inhaler. 315B is a calibrated orifice that will allow a very small known flow rate to the inhaler. For instance a 0.004" diameter orifice will allow a volume in one-half second of 21 ml for pure helium at 200 psig while 315A is a larger orifice, sealed by the secondary piston 313. Piston 313 is pushed against the casket 312 by the large diameter of the valve 311.

When the valve 311 is first pushed up, it pushes up piston 302, releasing high-pressure gas from the canister 301 to the outside via openings 309 and 310. The hollow diameter of piston 311 is now at the same level as the secondary piston 313. Aided by the spring 314, the piston 313 slides towards the valve 311 opening channel 315A. High-pressure gas flows via both orifices 315A and 315B producing the large amount of gas needed for the purge bolus. When the second volume of gas is desired, the valve 311 is pushed farther up. Due to the expansion in the valve diameter, the piston 313 is pushed back against 312 sealing orifice 315A. High-pressure gas can only flow via the calibrated orifice 315B alone creating the small amount of gas needed to mix with and nebulize the drug. Valve 311 is then pushed back down, releasing piston 302, and sealing the canister 301.

Equalization chamber 34, after the process described above, now has a desired pressure of gas 54 within it. Upon actuation of inhaler 30, gas 54 will be utilized by being injected into a gas passage 62 of a medical storage or drum section 64. Referring now also to FIGS. 1 and 4-6, drum section 64 includes a housing 65 that contains a rotating drum 66 and includes gas passage 62. An elastic material 67 is disposed between drum section 66 and housing 65 so that drum 66 can rotate freely within housing 65 but still retain drugs stored therein. Drum 66 is made of plastic or coated plastic to decrease or eliminate static electricity, which can lead to agglomeration of particles of an injected drug. Drum 66 includes a plurality of tubes 68, 70 that are substantially cylindrical and extend longitudinally therethrough. Drum 66 further includes a substantially cylindrical bore 72 also extending longitudinally therethrough. Tubes 68 contain a powdered drug formulation to be administered to a patient, whereas tubes 70 are empty and hollow to allow communication of gas 54 from equalization chamber 34 to a spacer 96 so that spacer 96 can be rapidly filled with several hundred ml of Heliox prior to injection of the fluidized dry powder drug formulation into spacer 96.

FIG. 1 shows an embodiment where drum 66 includes tubes 68 and so an attached spacer is not pre-purged. This is especially useful when the spacer is small in size. FIG. 4 shows an embodiment of drum 66 that includes tubes 70.

FIG. 4A shows a cross sectional view along line A-A of FIG. 4. As shown in FIG. 4A, tubes 70 are empty and have a diameter that is larger than the diameter of tubes 68. Tubes 68 contain a powdered medication 76. The diameter of each tube 68 is dependent on the volume and weight of dry powder of a specific drug to be delivered. Both tubes 68 and 70 are packed within rotating drum 66 so as to maximize the amount of doses available per rotating drum. For each drug filled tube 68, there is a corresponding hollow tube 70. A preferred arrangement is for the drug filled tubes and hollow empty tubes to be arranged in pairs vertical to each other. A multitude of such tube pairs can exist.

Micronized dry powder drugs can be made in particle ranges from preferably slightly smaller than 1 micron to 5 microns. A fluidized particle range of less than 1 micron to 3 microns is most beneficial for optimal drug delivery to the deep lung for systemic diseases. However, particle sizes should be optimized for both the delivery system, i.e. the inhaler design, and the targeted location in the lung. Therapeutic drugs to treat the upper or middle lung for respiratory diseases, can be up to 5 microns in size in their final fluidized and delivered form.

Referring to FIG. 4, when rotating drum 66 is to be used, drum 66 is placed upon spindle 78 so that spindle 78 is inserted into bore 72 and drum 66 is coaxial with spindle 78. As indicated by arrows 82, rotating drum 66 is selectively placeable upon and removable from spindle 78. A plurality of ducts 80 are disposed between gas passage 62 and both tubes 68 and 70 so as to provide a gaseous communication between these elements.

Two ducts 80 may be used to feed Heliox from equalization chamber 34 to spacer 96 with gas flow occurring through ducts 80 first to tubes 70 and then to corresponding tubes 68. After the allocated number of tubes per one concentric ring has been emptied, the ducts are moved to a different concentric ring and corresponding tubes. This can be accomplished through a simple appendage on drum 66 engaging a switch, or, a contact switch operated by low level current. Alternatively, one duct 80 may provide gas to both tubes 68, 70 which is on an assembly that moves, and which changes position moving from one concentric ring of tubes to the other.

For example, this can be done by a set of gears (not shown). The multidose barrel will rotate after (or before) each use using a gear drive activated by an external trigger. Duct 80 will be moved gradually to an inner concentric tube (if the tubes are arranged in spiral form or to the next concentric filled tube if all the tubes are concentric). Duct 80 can be also dropped suddenly after completing most of one rotation. This is accomplished by removing the last tooth of a gear so that duct 80 can be forced into an inner track with the help of a spring (not shown.

In another embodiment of drum 66, illustrated in FIG. 5, all of the tubes 68 in drum 66 contain dry powder drug and there are no corresponding hollow tubes 70. Instead, Heliox used to prefill spacer 96 is channeled through a spindle 78 on which drum 66 is mounted and rotates. This allows for a doubling of the number of tubes in drum 66 that contain the dry powder drug formulation. In both embodiments, shown in FIGS. 4 and 5, tubes 68 shown in dark indicate tubes that still have medication 86*a* and 86*b* within them. Tubes 68 that are open indicate tubes that no longer have medication to be dispensed within them.

In this embodiment, only one duct 80 at a time need be coupled to a corresponding tube 68. This is because spindle 78 is used to provide communication of gas 54 with spacer 96. Additional ducts 80 could be used for a different concentric ring of tubes 68. The embodiment of FIG. 5 would increase the number of tubes containing drug powder or liquid in rotating drum 66, raising the multi-unit dose capacity of a single disposable plastic barrel.

Figure 5:
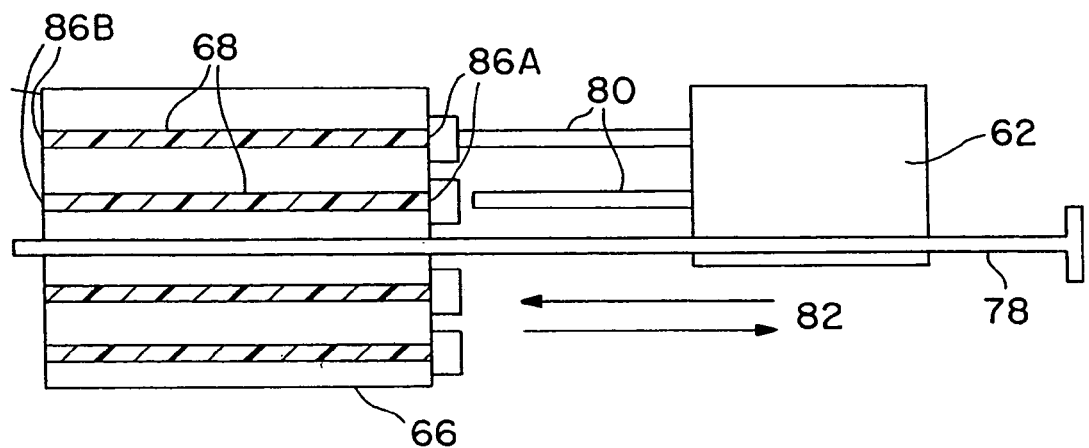
FIG. 5 is an alternative to FIG. 4.

If the embodiment of FIG. 5 were used, ducts 80 would act as a source of propellant and fluidizing energy for the drug in the tubes. Each duct is activated by a mechanical means when the ducts are to be utilized. Alternatively, a single Heliox source needle can change position to access each circular row of drug bearing tubes in succession.

Figure 4:
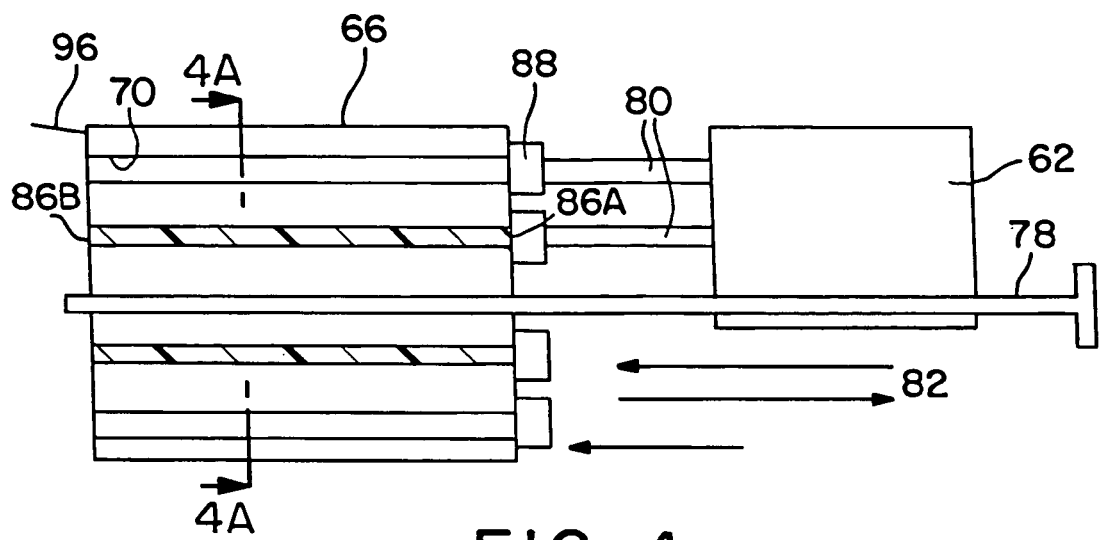
FIG. 4 is side view of a drug drum assembly.
Figure 4A:
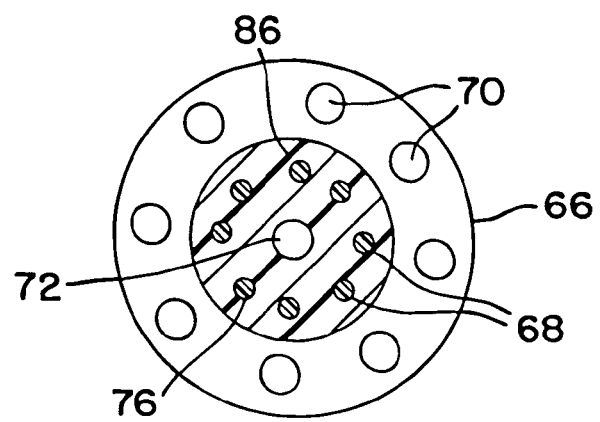
FIG. 4A is a sectional view of A-A of the drum of FIG. 4 used to hold a drug in accordance with the invention.

As shown in FIGS. 1, 4 and 5, a clear sealed plastic overlay 86 is disposed on the front 86a and back 86b of drum 66 covering all tubes 68. Plastic overlay 86 contains and protects the dry powdered drug 76 from moisture, provides an anti-microbial barrier, and keeps tubes 68 clean and moisture free for pre-dose generation of Heliox gas injection into the spacer 96.

Plastic overlay 86 will have a surface strength marginally less then the pressure of gas 54. When gas 54 is injected into drug filled tube 68, plastic overlay 86a bursts inward into tube 68. A buildup of pressure from Heliox 54 then occurs in tube 68, and explosively blows plastic overlay 86b-existing on the spacer side of tube 68 thereby fluidizing powder 76 into the environment of the spacer.

Figure 6:
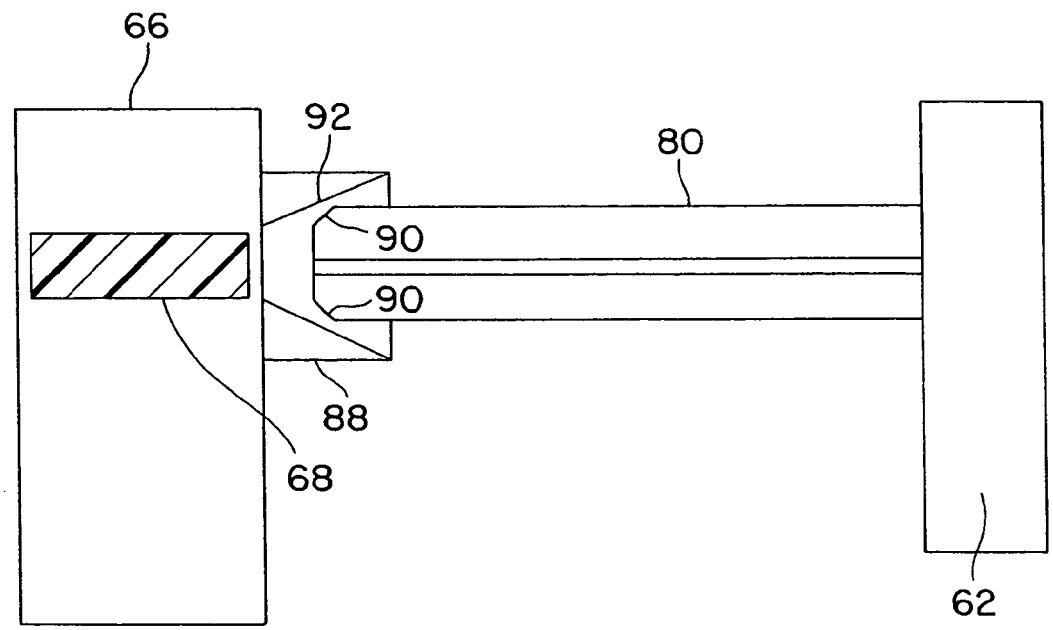
FIG. 6 is a side view showing the engagement of the drum and an equalization chamber.
Figure 7:
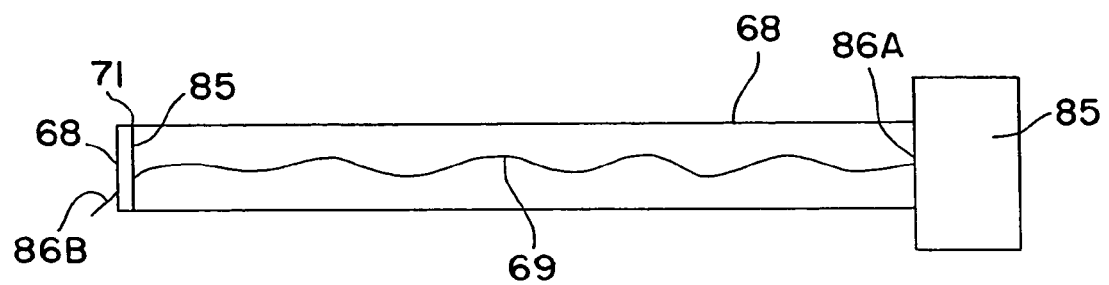
FIG. 7 is an enlarged side view of a tube containing a liquid drug.
Figure 8:
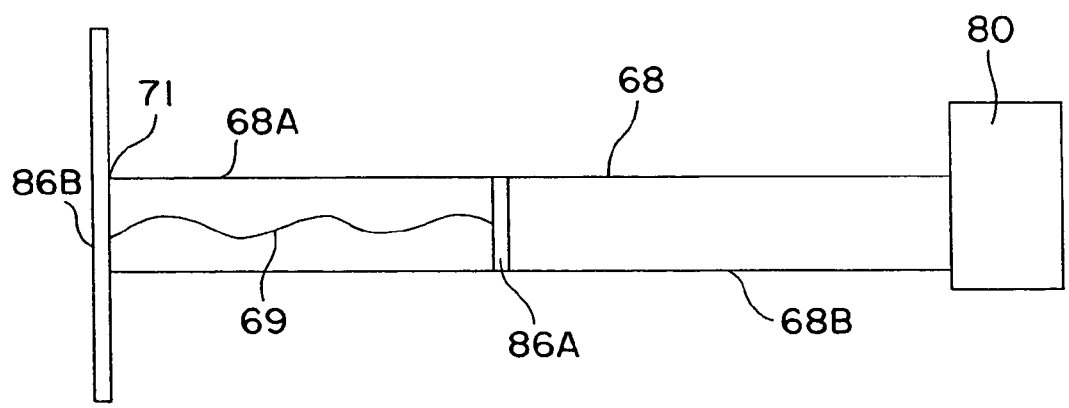
FIG. 8 is an enlarged side view of an alternative embodiment of a tube containing a liquid drug.
Figure 9:
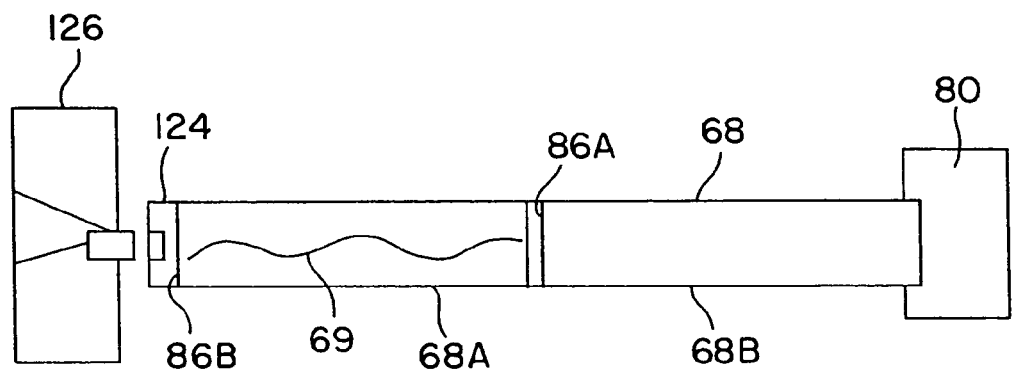
FIG. 9 is a side view of a tube adapted to be coupled to a fixed nozzle.
Figure 10:
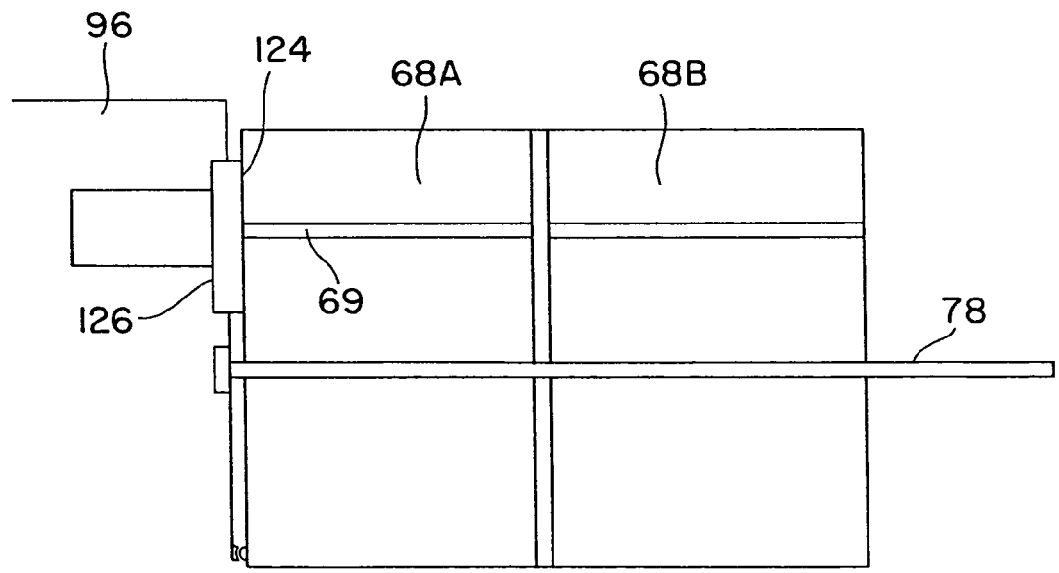
FIG. 10 is a side view of an alternative coupling of a tube with a fixed nozzle.

The engagement of rotating drum 66 with ducts 80 is illustrated with reference to FIG. 6. Rotating drum 66 includes a receptacle 88 for hermetically receiving duct 80 therein. Rotating drum 66 can be designed so that plastic overlay 86*a* covers the entire front of rotating drum 66 and receptacle 88 is affixed over plastic overlay 86*a*. Alternatively, receptacle 88 may have a plastic membrane similar to plastic overlay 86 built into it. Duct 80 includes beveled portions 90 made of a strong but pliable material so that when ducts 80 are inserted into receptacle 88, a small amount of physical pressure is required to maintain a tight friction based seal between receptacle 88 and duct 80 during injection of the Heliox gas. Receptacle 88 further has a trapezoidal shaped appendage 92 designed to accept duct 80 on a hermetic fitting basis at the pressure required for operation and drug powder fluidization.

Alternative embodiments of rotating drum 66 are shown in FIGS. 7 and 8 where tubes 68 may contain, instead of powdered drug 76, a liquid drug 69 disposed therein. In the embodiment shown in FIG. 7, a micropore aerosol nozzle 71 is disposed in tube 68 at an end opposite duct 80. As with the prior embodiments, plastic overlay 86 keeps liquid drug 69 within tube 68 until it is desired that liquid drug 69 be administered. In this embodiment, a space 85 is provided between aerosol nozzle 71 and plastic overlay 86B. Space 85 could be 0.25 inches or larger. Aerosol nozzle 71 is a hard structure with micropores. Plastic overlay 86B will expand and stretch before it ruptures so it should not lay on top of the aerosol nozzle 71. Space 85 will also prevent plastic overlay 86 from sticking over aerosol holes in aerosol nozzle 71 when plastic overlay 86 ruptures.

Referring to FIGS. 9 and 10, another embodiment of tube 68 is shown. In this embodiment, again tube 68 is divided into a liquid container part 68*a* and gas conveyer part 68*b*. Liquid drug 69 is contained within liquid container part 68*a* through the use of plastic overlays 86*a, b*. Tube 68 further includes a friction seat 124 that is designed to selectively mate with a fixed nozzle 126 of spacer 96. In FIG. 10, spindle 78 is shown as the conduit for compressed gas 54. It should be clear though that tubes 70 could also be used in a drum 66 that has a friction seat 124 which mates with a friction nozzle 126.

In the embodiments shown, where a fixed nozzle is implemented, when drum 66 rotates to align a new drug to be administered, drum 66 is moved forward toward spacer 96 and press fitted therein. This forward performed movement may be accomplished mechanically or manually by the patient.

In all of the embodiments discussed above, when gas 54 is applied to tube 68, the application causes an explosion of plastic overlay 86*a* blowing into chamber 68. This explosion, combined with the combination of gas pressure plus drug 69, 76 inside tube 68 bursts the plastic overlay 86*b* covering the other side of tube 68. This bursting of plastic overlay 86 provides a large explosive and subsequent turbulent effect to fluidize powder 76 or aerosolize liquid drug 69. The drug-Heliox combination is then introduced to a spacer 96 (FIG. 1), which has an environment of about 270 ml of Heliox gas. An advantage of this method, is that the ducts do not have to penetrate a pre-scored vapor barrier which might clog the duct but instead the ducts provide a gas to blow out the plastic overlays based on a predetermined plastic film strength and gas pressure.

Disposable multidose drum 66 is designed so that it can only be inserted onto spindle 78 on which it rotates in the correct manner. That is, a position where the front of the drum 66 is inserted correctly juxtaposed to where the Heliox source (s) ducts are located.

Referring now to FIG. 1, the operation of inhaler 30 will now be explained. An activating trigger 94 is disposed on drum section 64. Trigger 94 can have several stops like a multi-action pistol trigger, or may have an activating button plunger with the same multi-action inducing activities. When trigger 94 is depressed, drum 66 is rotated about spindle 78 to a correct position for the next dose. An inhalation port door 98 coupled to a mouth piece 99 of spacer 96 closes, thereby inhibiting a user from inhaling gas disposed within spacer 96. Alternatively, inhalation port door 98 could be first left open so that the air in spacer 96 is more efficiently purged out (as discussed immediately below). Thereafter, inhalation port door 98 is closed as above. Yet another embodiment includes using a combination pressure/vacuum port (not shown) which opens to let air out during the purging phase and closes during the drug delivery phase.

If an embodiment shown in the drawings is used, a quantity of 230-270 ml of Heliox gas is injected into spacer 96 from equalization chamber 34 to gas passage 62, through tubes 70 or spindle 78, through another gas passage 63 (not shown in figures) in housing 65 and finally through a compressed gas input port of spacer 96. The air in spacer 96 is pushed out or purged through a pressure port 100 so as to assure as close to a 100% Heliox is present in the ambient spacer environment as possible. The Heliox gas provides both a spacer environment for settling of the heavier undesirable particles, and provides a large bolus front wave of gas in which the desired fine particle fraction will be entrained during inhalation. This will provide a sufficient amount of volume of Heliox gas to have the desired effect on delivery of particles in to the deep lung.

In the embodiment shown in FIG. 1, the spacer 96 is not necessary pre-purged. Therefore, all the volume of Heliox in the equalization chamber is used to fluidize and deliver the drug only. If pre-purge is desired, the first volume of Heliox delivered by any option presented in FIGS. 2 and 3 is first sent through the tubes 70 or 78 to purge the inside of spacer 96 then drum 66 rotates, allowing the second volume of Heliox to nebulize the drug. A double action trigger can be used to activate the process in sequence as presented in FIGS. 2 and 3.

When the process of filling spacer 96 with gas 54 ends, inhaler 30, based on a sequence automated or manually activated by trigger 94, shoots 30 to 70 ml of gas 54 obtained via the options presented in FIGS. 2 and 3 into tube 68 containing the drug formulation. The gas fluidizes powder drug 76 (or aerosolizes drug 69), driving the drug through drug input port 68 into spacer 96, and causes turbulence which helps to further fluidize and deagglomerate the drug. In fact, one port could be used to deliver both the compressed gas alone, and a combination of the compressed gas and drug.

Alternatively, Heliox gas 54 used to aerosolize drug 76 or 69 may be provided in two pulses, of, for example, 60% and then 40% of the total intended volume. This procedure assures all powder 76 from tube 68 is injected into spacer 96, and further adds turbulence to spacer 96 so that the particles are kept separated.

At a pre-determined period of time thereafter, e.g. 0.5 to 5 seconds, a mechanical timer opens inhalation port 98 so that the patient can inhale cloud of particles. A combination of a spring, gear and wire (not shown) attached to trigger 94 can be used to make inhalation port door 98 close when trigger 94 is depressed. Depressing trigger 94 also activates the Heliox purge at the same time. When the patient releases trigger 94, the spring, gear and wire open inhalation port door 98 and start the drug delivery. A vacuum/pressure valve 104 will close automatically until inhalation door 98 opens and will equalize the pressure inside spacer 96 until the patient has finished inhaling.

As the patient inhales cloud of particles, a vacuum begins to form in spacer 96. At a certain pressure, vacuum/pressure valve 104 opens allowing ambient air into spacer 96. By opening vacuum/pressure valve 104, the patient may continue a steady deep inhalation of room air following the Heliox bolus, slug or gas front entraining particle cloud.

Vacuum/pressure valve 104 also ensures that larger particles that may settle on the bottom of spacer 96 do not get inhaled by a user. Vacuum/pressure valve 104 can be opened/closed automatically. For example, it can be made of a piece of flexible metal strip. At atmospheric pressure, the strip will line up perfectly with the wall of spacer 96. When the Heliox builds up excess pressure during purging, vacuum pressure valve 104 will coil upward, keeping the Heliox in. When inhalation port door 98 is opened by the trigger wire, the pressure will drop to normal. During the drug delivery, the patient will breathe in much larger volume of gases (500 ml to 1.5 liters) than the 230-270 ml. During the inhalation, a vacuum will form as the Heliox with the drug will be inhaled. Now the metal strip will coil inwards to allow air to rush in.

This structure prevents excess pressure or velocity of the Heliox/drug combination. Moreover, since the whole process occurs within a few seconds, it is not necessary to make the system leak proof or strong enough to sustain any particular high pressure.

Spacer 96 provides the following benefits:

a) slows down the velocity of the Heliox gas plus drug formulation injected into the spacer;

b) allows sufficient turbulence to keep the small desirable particles suspended and separated;

c) allows the heavier particles unsuitable for pulmonary drug delivery to settle out or be trapped in the spacer; and d) provides a bolus, slug or initial front of gas plus drug formulation that is 100% Heliox, followed, thereafter, by air as part of the same continuous breath.

Spacer 96 may be further provided with a scented receptacle 110 disposed on an upper and outer part of the spacer near to where a patient's nose would be.

Receptacle 110 may be a scented strip containing essence of vanilla, mint, or another scent, and is placed near the nose to make the use of the inhaler pleasant for children and older adults who dominate the usage population.

Spacer 96 should be constructed of a plastic, or provided with an inner coating, that eliminates the generation of static electricity. This is because static electricity imparted to the drug particles injected into the spacer could result in clumping and adversely affect the dose delivered to the patient.

It is desirable for spacer 96 to incorporate in its inhalation port door 98 an apparatus to prevent the accidental exhalation by the patient into spacer 96 prior to inhalation, so as to avoid mixing of exhaled gases with the Heliox and suspended drug cloud of particles, and to avoid agglomeration of the particles due to exhaled moisture. It is also desirable for inhalation port door 98 to be closed upon introduction of the Heliox ambient atmosphere and Heliox plus drug formulation into spacer 96, so that only Heliox is in spacer 96 and a minimal amount of that Heliox is lost external to spacer 96.

Spacer 96 can be made of rough materials on its surface. The rough surface serves two different purposes. It can slow down the Heliox-powder mixture to a laminar flow by inducing additional boundary layer drag force. The rough surface can also provide a trap to hold the large particles.

After the injection of the Heliox gas and Heliox plus drug formulation into the spacer, it is further desirable to reduce the Heliox velocity immediately prior to transit from turbulent flow to laminar flow. An impact plate (ball or other object) and a diffuser can accomplish this reduction in velocity. Referring again to FIG. 1, a diffuser 112 is disposed between spacer 96 and drum section 64.

Diffuser 112 includes an impact ball 114 at a portion of diffuser 112 that is proximate to gas passage. Impact ball 114 is used to reduce the initial high velocity of highly turbulent gas and drug that enters diffuser 112. When gas and drug is injected into diffuser 112, a high-energy flow may concentrate in the center of the unit. Impact ball 114 helps avoid this channeling effect. Diffuser 112 is shaped as an expansion cone to slow down the gas-powder mixture. The size of diffuser 112 is dependent on the desired gas-powder mixture velocity hitting the back of the throat. The velocity should be low enough so that the flow is laminar. At an inhalation flow rate of 60 L/min (often the necessary flow rate required by some DPIs to release the drug), the Reynolds number is 670 for pure helium compared to 5,400 for air. Using a certain mix of helium and air changes the Reynolds number accordingly, as shown in Table 2. Even if the Reynolds number is low enough so that it falls into a laminar category, the flow might still be turbulent due to the roughness of the surface for instance. Spacer 96 can be combined with diffuser 112 so that the large particles can drop out of particle cloud in spacer 96.

TABLE 2

Effect of concentration of helium on flow regime.

| | Percentage of Helium (balance oxygen) | | | | | |
|---|---|---|---|---|---|---|
| % Helium | 0 | 20 | 40 | 60 | 80 | 100 |
| Diameter of throat (cm) | | | 1.8 | | | |
| Inhalation rate (L/min) | | | 60 | | | |
| Velocity (m/s) | | | 3.9 | | | |
| Gas density (g/cc) | 1.43 | 1.18 | 0.93 | 0.68 | 0.43 | 0.18 |
| Viscosity (μP) | 204 | 201 | 198 | 196 | 193 | 190 |
| Reynolds number | 4950 | 4140 | 3310 | 2460 | 1670 | 666 |
| Flow Regime* | T | T | T | Trans | Trans | L |

*T = Turbulent, Trans = Transitional, L = Laminar

The function of impact ball 114 can be incorporated into spacer 96. Spacer 96 could include an impact plate disposed at an end of spacer 96 proximate to inhalation port door 98. In this design, the injected Heliox stream and drug particles would hit impact plate causing impaction and turbulence, and resulting in a reduction in the velocity of particle cloud. The impact plate could be tilted so that the injected Heliox and drug particles would reflect off impact plate, thereby resulting in the accelerated settling of heavier particles and the formation of a cloud of desired particles containing a desired fine particle fraction.

Diffuser 112 and spacer 96 can also include a flow-straightening device. For example, diffuser 112 and spacer 96 can be sub-divided into parallel channels. The channels will adsorb all the energy from the random motion of a turbulent flow.

Figure 11:
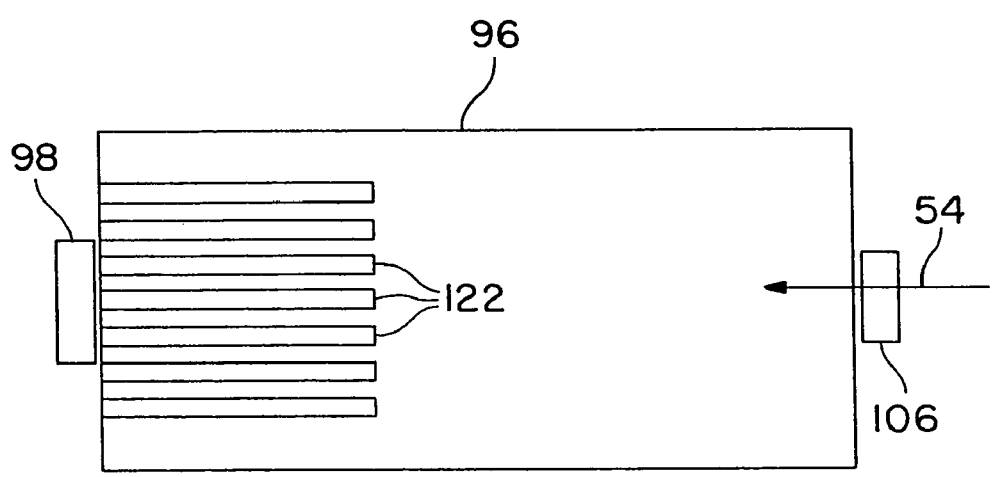
FIG. 11 is a side view of a spacer in accordance with the invention.

Referring to FIG. 11, there is shown a flow straightening device that can be used in spacer 96. Spacer 96 further includes a plurality of shelves 122 disposed proximate to inhalation port door 98. Shelves 122 function so that gas 54 passes over or just above and below shelves 122, thereby helping to induce a straightened flow of the Heliox and entrained particles into the patient.

It should be made clear that spacer 96 and diffuser 112 are merely additional options that could be used with inhaler 30. A patient may use spacer 96 only, diffuser 112 only, or neither appendage when using inhaler 30. If spacer 96 is not used, mouthpiece 99 should be placed on the end of diffuser 112. If diffuser 112 is also not used, then mouthpiece 99 should be placed on an end of gas passage 62. It should also be clear that when mouthpiece 99 is not disposed on spacer 96, it is not necessary to further include inhalation port door 98.

Figure 12:
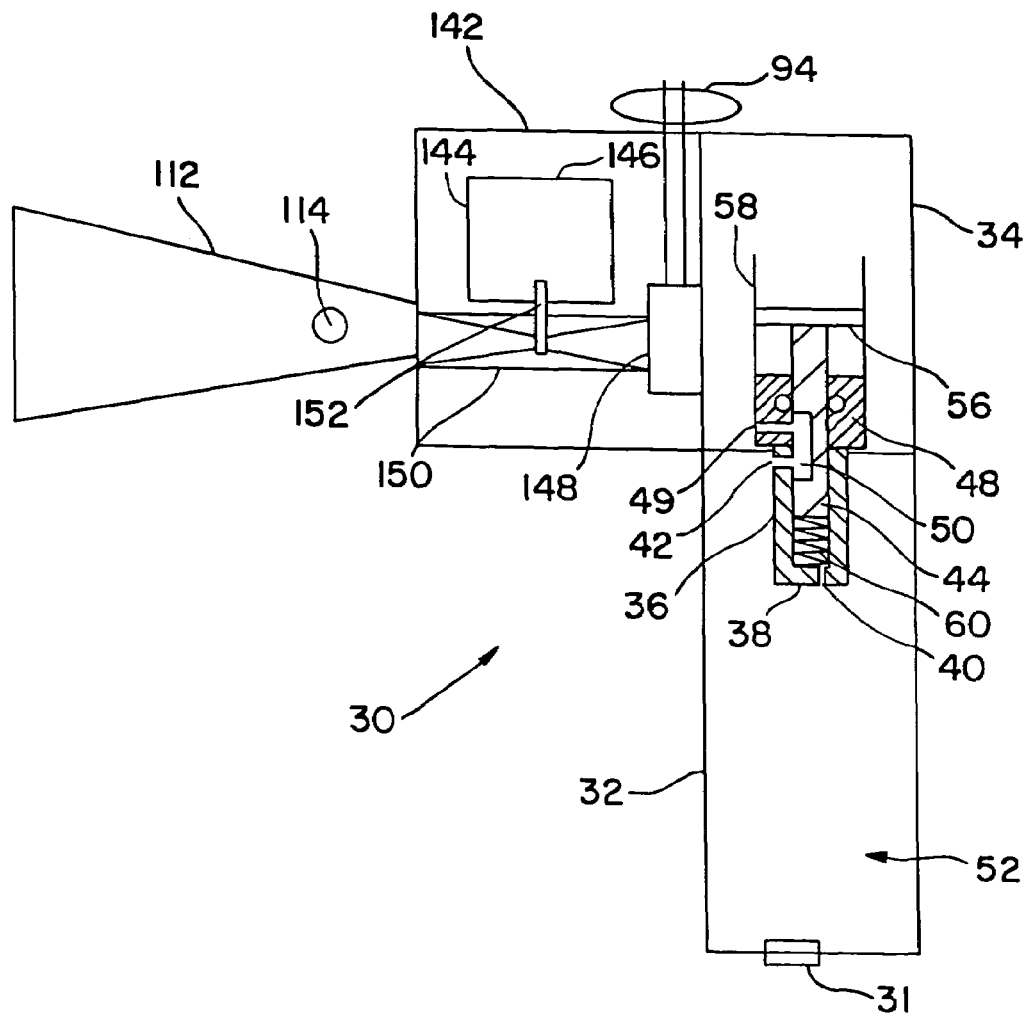
FIG. 12 is a side view of another embodiment of an inhaler and diffuser in accordance with the invention.

Referring to FIG. 12, there is shown another embodiment of the invention. Similar elements contain the same reference numerals described above and their description is omitted for the sake of brevity. The inhaler comprises, a venturi section 142 coupled to chamber 34. Venturi section 142 includes a liquid drug reservoir 144 having a store of liquid drug 146 contained therein. A gas passage 148 selectively provides communication between equalization chamber 34 and a venturi 150. The inlet of venturi 150 communicates with gas passage 148. The outlet of venturi 150 communicates with diffuser 112. The throat of venturi 150 communicates with a liquid metering tube 152 coupled to liquid drug reservoir 144.

As would be understood by one with ordinary skill in the art, when gas 52 passes through venturi 150, since the throat of venturi 150 is constricted, a decrease in pressure of gas 54 is experienced at the throat of venturi 150. This apparent vacuum sucks a quantity of liquid drug 146 out of liquid drug reservoir 144. This quantity of liquid drug 146 is aerosolized by gas 54 and injected into diffuser 112. Clearly, diffuser 112 is not necessary as the gas/drug combination could go directly to spacer 96 or to the patient.

Another embodiment of the invention would use ultrasonic nebulization. Ultrasonic nebulization is more efficient in delivering properly sized particles and reducing dead (unused) volume of medication. Its main disadvantage comes from an increase in temperature over long use. This is avoided in the present invention since the nebulization will only occur via short puffs. Although not as extensively used as the Venturi principle, it is in the core of new inhaled drug delivery systems such as the AeroDose (AeroGen Inc, Sunnyvale, Calif., patent U.S. Pat. No 474,536), Premaire Metered Solution Inhaler (Sheffield Pharmaceuticals), or the Vibrating Membrane Nebulizer (Pari GmbH, Germany). Ultrasonic nebulization uses the excitation of a piezoelectric crystal vibrated at high frequency to create waves in the liquefied drug solution placed directly above the crystal. The oscillation waves then disrupt the surface and create a geyser-like behavior at the surface, nebulizing the drug that is then carried by the Heliox gas passing above the surface on its way to the spacer. The practical means is not specifically addressed here, only the concept of adding ultrasonic nebulization to the helium/Heliox inhaler is presented. Ultrasonic nebulization can easily be adapted to the present invention.

In all of the above arrangements, the spacer is designed to accommodate the total volume of Heliox gas to be injected into it both as a bolus of gas and with the drug dose. The spacer is designed so that the Heliox gas displaces the ambient air that is in the spacer prior to the introduction of Heliox and then replaces it with Heliox gas and drug formulation.

Sufficient gas pressure is needed to optimally fluidize the powder (or aerosolize the liquid drug) in a manner that particles of the desired size range and grouping are generated. Therefore, it is desirable to have a cut off pressure valve which, when the pressure in equalization chamber 34 is insufficient to provide sufficient Heliox volume to fill spacer 96 and a pressure wave to optimally fluidize or aerosolize the drug, the inhaler will cease to function. Such a cut off switch could be comprised of a pin hook that is effective to disengage trigger 94. Pin hook could be coupled to a spring that could be in turn coupled to a diaphragm. Thus, when the pressure in equalization chamber 34 is high enough, the diaphragm would be pushed towards equalization chamber 34 thereby elongating the spring. This elongation of the spring clears the hook from trigger 94 and allows trigger 94 to operate. When there is insufficient pressure in equalization chamber 34, the hook engages trigger 94 and thereby precludes trigger 94 from operating. Another embodiment includes employing a pre-calibrated Heliox gas cylinder that will provide more than enough Heliox for all the medication inside drum 66. Furthermore, a pressure activated flag or signal, could be implemented to tell the user that a cartridge needs to be replaced.

Since it is critical that patients have access to medication when needed, a counting method is desired concerning the number of doses remaining. A counting method can be placed above or by each drug tube in drum 66 with an indicator for indicating the number of doses left. Each application of trigger 94 will rotate drum 66 once and when the medication is empty, the indicator on drum 66 would indicate that there is no medication left in the device.

As the inhaler in accordance with the invention can deliver different drugs by use of different multidose drug drum, a clear label with black letters stating the drug and potency and a color band coding system can be affixed to the outside of each drum. This clear label material will not obstruct the contents of the tubes within the barrel containing the drug formulation. These features also provide an added safety measure by allowing a visual verification of remaining doses, in addition to one provided by a simple automatic counting mechanism which is a part of the device which tells the user how many doses have been used, or how many doses are left. The "zeroing" of said device can be done manually, or, be automatically done by a feature of the barrel such as an appendage.

One advantage of this system, is that drug containing tubes in a single disposable multi unit dose barrel can contain the same drug, or, a sequence of drugs to be taken over the course of a day. For example tubes 1, 2, 3, 4 may contain a sequential medication group and tubes 5, 6, 7, 8 a repeat of the same medication group with each dose, for example, within tubes 1-4 to be inhaled every 6 hours.

Examples of classes of drugs being investigated and formulated for pulmonary administration, which may be administered with the invention, include, but are not limited to, those for chronic obstructive lung diseases such as the classes of agents commonly referred to as anticholinergic agents, beta-adrenergic agents, corticosteroids, antiproteinases, and mucolytics, and include such specific drugs.

Other therapeutic pharmaceuticals for respiratory disease use in dry powder and/or liquid form with which the invention could also be used include, but are not limited to, benzamil, phenamil, isoproterenol, metaproterenol, Beta 2 agonists in general, Proctaterol, Salbutamol, Fenoterol, ipratropium, fulutropium, oxitropium, beclomethasone dipropionate, fluticasone propionate, salmeterol xinafoate, albuterol, terbutaline sulphate, budesonide, beclomethasone di propionate monohydrate, surfactants such as colfosceril palmitate, catty alcohol and tyloxapol, P2Y2 agonist (rapid stimulates mucus and is potentially for use in CORD and OF), aerosolized dextran (for OF), and mannitol powders (for bronchial provocative challenge). An example of another therapeutic drug that could be delivered by the invention is Pentamidine for AIDS related therapy.

Examples of proteins and peptide hormone drugs that may be administered with the invention, which may or may not be glycosolated, include somatostatin, oxytocin, desmopressin, LHRH, nafarelin, leuprolide, ACTH analog, secretin, glucagon, calcitonin, GHRH, growth hormone, insulin, parathyroid, estradiol and follicle stimulating-hormone and prostaglandin El.

In addition, genes, oligonucleotides, anti-coagulants such as heparin and tPA, anti-infective to treat localized and systemic bacterial or fungal infections, enzymes, enzyme inhibitors, vaccines, anesthetics, pain killers, and agents that can turn certain types of receptors on, off, or enhance their response are possible therapeutic drugs or action inducing substances which may be delivered via the invention.

Ergotamine for the treatment of migraine headaches and nicotine to substitute for and eventually eliminate cravings for tobacco, are also therapeutic formulations that may be administered by the invention, along with insulin.

Furthermore, controlled release drugs such as those that are liposome based and which are designed for pulmonary drug delivery to treat respiratory and systemic diseases over a period of time due to the chronic nature of the illness or the mode in which the illness responds to medication, or the mode in which the medication operates, may be administered by the invention.

Existing DPIs use the patient's inhalation alone, the patient's inhalation assisted by a propeller, or compressed air generated by a hand pump in a DPI, to fluidize the dry powder drug formulation. One DPI also uses compressed air in a plastic pillow that contains the dry powder drug formulation as an aid to fluidization.

The present invention offers several advantages over these approaches to fluidizing a dry powder drug formulation. First, the volume of gas (Heliox) and its pressure are independent of the operator's inhalation velocity, ability to generate a given level of inhalation velocity (if, as in some devices, a minimum threshold is required for release of the powder for fluidization), or physical motion. No batteries need to be checked and replaced periodically as is required for the propeller driven system. Compressed air does not have to be pumped prior to each dosing.

DPIs that rely on inhalation power, a propeller, or hand pumped compressed air, all use air that is from the environment where the user is present. If the air is humid, it can cause clumping of the micronized dry powder drug formulation, resulting in larger particles that may not reach the upper lung, let alone the deep lung. A factory produced compressed Heliox source can be produced as a desiccated dry gas, eliminating this problem in humid climates. This in turn, would cause variability in the fluidization, deagglomeration, and post clumping of dry powder drug formulations, which in turn effects the fine particle fraction available for pulmonary administration and effective therapy.

A factory-produced source of pressurized Heliox also provides the advantage of a high velocity gas stream, which provides the advantage of a more forceful impact on and fluidization of a dry powder drug formulation, compared to the force generated by inhaled air, battery powered propeller assisted air, or hand pumped compressed air. The result is that the powder can be fluidized and deagglomerated more completely, with the result being a more consistent and effective use of a unit dose of the formulation, and potentially a reduction in the nominal drug powder formulation that must be loaded into the inhaler as more is consistently deliverable.

The use of tubes, instead of blisters and reservoirs of powder as in the prior art, allows the effect of the gas pressure to be magnified in terms of velocity generated and impact of the gas on the particles.

The use of a multi-unit dose disposable drum with preloaded tubes of drug formulation prepared under factory controlled conditions, is an improvement over the prior art, which uses a barrel permanently open on one end, into which the user must insert capsules, and after use, remove the capsules. First, there is the factor of user variability in loading the capsules in the prior art, and of loading the right capsules if a user takes more than one medication that may be administrable by the system. Second, powder can remain in the capsule and tube due to physical obstruction of airflow by the debris after the capsule is punctured. Third, because the broken capsules have to be removed by the user as the barrel is fixed and not merely used and disposed, there is also residual powder in the tube. This residual powder can alter the dose delivered to the patient when another capsule is put into that tube and used, or, worse, if another medication is administered, the two powders might mix with an unknown variable, or perhaps undesired effect on the patient system.

Another advantage of the compressed low molecular weight Heliox gas is that it can also be used for delivering liquid drug formulations. Heliox is a much better liquid aerosolizing/atomizing agent because of its high velocity of release and it does not have the same cooling characteristics of liquid CFCs.

In the present invention, the multidose insert containing multiple sealed unit doses of liquid drug, or a reservoir multidose liquid drug source, is stored separately from the compressed gas. In contrast, in MDIs, the propellant and drug formulation are stored together, along with many other additional additive ingredients. In the case of liquid drug suspension formulations, the MDI must be shaken before each use to try to achieve a uniform consistent dosing. Additionally, temperature changes can make the drug compound, which is packaged with the propellant, come out of solution.

The uniquely designed spacer reduces the high velocity of the Heliox gas and the dry powder particles or aerosolized droplets of liquid drug that have been generated, resulting in the desired settling within the spacer of the larger particles which are neither desirable nor effective for pulmonary drug delivery. Existing spacers are filled with ambient air prior to the entrance from the MDI or DPI of air plus entrained drug powder or liquid drug droplets.

In the present invention, the spacer is pre-filled with Heliox gas prior to the mixture of Heliox gas and entrained drug powder or liquid droplets entering the spacer. This provides a unique gas environment for a) a differential settling of heavier particles than air, and b) a large volume bolus of Heliox plus a desired fine particle fraction which is then inhaled by the patient, followed on a continuous inhalation basis with air, with the Heliox and particles being the inhaled tidal gas front. The spacer also can have laminar flow shelves, which help induce the laminar flow of Heliox plus entrained particles from the "cloud" of fluidized powder or aerosolized liquid drug formulation upon inhalation by the patient. The spacer reduces the velocity of the gas stream to an acceptable cloud of particles, the undesirable particles settle out, and the resulting cloud of remaining particles that are of the desired particle size range can be inhaled. The laminar flow shelves aid in the introduction of a laminar flow out of the spacer of the helium gas and entrained particles.

Then, upon inhalation, it is highly desirable to keep the particles of the desired size range from settling. With viscous drag greater than the gravitational settling velocity, the fine solid particles can be suspended indefinitely without settling. On the other hand, additional viscous drag will cause an excess pressure drop. It is therefore, desirable to control the viscosity.

The ability of this invention to generate initial high turbulent flow and provide rapid flow deceleration is important to the performance of the inhaler for powdered drug delivery.

A high pressure chamber and an equalization chamber are provided so that Heliox gas can be stored efficiently under a high pressure and also be used as a propellant to fluidize or aerosolize a drug at a lower pressure. Using a mechanical way to systemically provide two widely different volumes of gas allows to create first a bolus of gas then a second volume of gas to fluidize, nebulize the drug, independently of a variable user activation. By providing a disposable chamber for storing medication, a user does not have to manually insert and remove drugs and there is no concern that the tubes carrying these drugs will become soiled from prior administered medication. By injecting a hermetically sealed spacer with some Heliox prior to injecting the same spacer with a Heliox/drug combination, the heavier particles in the Heliox/drug combination can be settled quicker than in air. Also, a large volume bolus of Heliox plus a desired fine particle fraction can be inhaled by the patient, followed by inhalation of air, with the Heliox and particles being the inhaled tidal gas front. The drug/Heliox combination in the spacer is also less susceptible to external factors such as humidity in the ambient air as the spacer is hermetically sealed. Finally, by using Heliox as a propellant, a drug fluidized or aerosolized by this propellant has a better chance of navigating the airways and reaching desired portions of the lung.

The main costs of the inhaler are the drug and the manufacturing/parts. The cost of Heliox, while being an expensive gas by itself, is less than the other costs. There is then an incentive for the patient to be able to use the inhaler for a much longer period than the limited number of doses available in the canister. Providing the user with an in-home mean to refill his canister allows him to continue using his inhaler for longer periods of time without going to the pharmacy or doctor. The higher cost of the inhaler would then be paid for by the longer use.

While preferred embodiments of the invention have been disclosed, various modes of carrying out the principles disclosed herein are contemplated as being within the scope of the following claims. Therefore, it is understood that the scope of the invention is not to be limited except as otherwise set forth in the claims.

What is claimed is:

1. An inhaler for introducing a drug into a user, said inhaler comprising:

a first chamber containing a first compressed gas at a first pressure, said first chamber being substantially free of any drug;

a second chamber in selective flow communication with said first chamber, said second chamber containing a second compressed gas at a second pressure lower than the first pressure and said second chamber being substantially free of any drug, said first and second chambers cooperating so as to yield said second pressure of said compressed gas within said second chamber;

a means for delivering two different volumes of gas in successive applications from the second chamber to a storage section, said storage section storing the drug to be administered, wherein said successive volumes of gas fluidize and aerosolize said drug and produce a drug cloud;

a mouthpiece coupled to said storage section, said mouthpiece adapted to receive said drug cloud and convey said drug cloud to the user;

a first housing disposed within said first chamber; a second housing disposed within said second chamber having an opening therein; and a piston slidably disposed within said first and second housings.

2. The inhaler of claim 1 wherein said first chamber contains a first compressed gas compressed between about 50 and about 4000 psig, and said second chamber contains a second compressed gas compressed between about 20 and about 100 psig.

3. The inhaler of claim 1 further comprising:

a first housing disposed within the first chamber, said first housing having a first opening therein, said first housing defining a third chamber internal to said first housing; and the piston having a third opening therein; wherein said first, second, and third openings are arranged so that a first position of said piston within said first and second housings selectively allows said communication between said first chamber and said second chamber and a second position of said piston within said first and second housings does not allow said communication between said first and second chambers.

4. The inhaler of claim 3 wherein said piston is coupled to said second chamber through a biasing member so that said piston is biased toward said first chamber.

5. The inhaler of claim 4 wherein:

said first chamber contains the first compressed gas and said first compressed gas applies a first force upon said piston toward said second chamber; and said second chamber contains the second compressed gas and said second compressed gas applies a second force on said piston toward said first chamber; and said first force, and said second force along with a third force due to a spring in the first housing ensure that said second compressed gas is disposed in said second chamber at said second pressure.

6. The inhaler of claim 1 wherein said means for delivering two volumes of high-pressurized gas from said second chamber occurs due to an specially shaped piston allowing successive communication between two chambers of different capacity.

7. The inhaler of claim 1 wherein said means for delivering two volumes of high-pressurized gas from said second chamber occurs due to different gas in a first orifice and a second orifice.

8. The inhaler of claim 7 wherein said first orifice chamber is a calibrated orifice so to deliver a selected amount of gas.

9. The inhaler of claim 7 wherein second orifice is larger than said first orifice and selectively opened by a piston to deliver a larger amount of gas than the gas in the first orifice.

10. The inhaler of claim 7 where the opening of the first and second gas orifices is selected by the movement of a piston.

11. The inhaler of claim 1 wherein said storage section is in the shape of a drum and comprises:
    at least one first tube extending through storage section and adapted to allow the second compressed gas to pass therethrough; and
    at least one second tube extending through the storage section, with said second tube adapted for containing the drug therein.

12. The inhaler of claim 11 wherein:
    said second chamber further includes at least one duct extending therefrom; and
    said at least one duct is coupled to said storage section with said duct adapted for providing gaseous communication from said second chamber and said storage section.

13. The inhaler of claim 11 wherein said second tube is comprised of at least a first and second part mateable together, with said first part adapted for containing said drug and having a sealing overlay at its ends thereof.

14. The inhaler of claim 11 wherein a drug in a liquid or powder form is stored in said second tube.

15. The inhaler of claim 14 wherein said second tube further comprises an aerosol nozzle at an end thereof.

16. The inhaler of claim 14 wherein said second tube further includes a friction seat at an end thereof and a fixed nozzle is mateable with said friction seat to provide communication between said second tubes and said mouthpiece.

17. The inhaler of claim 14 wherein said second tube has an end coupled to a fixed nozzle to provide communication between said second tube and said mouthpiece.

18. The inhaler of claim 1 wherein said second chamber further includes a hollow spindle extending therefrom and said spindle coupled to and extending through said storage section to provide gaseous communication from said second chamber to said storage section; and
    said storage section includes a tube extending through said storage section and said tube adapted for containing a drug therein.

19. The inhaler as claimed in claim 18 wherein:
    said second chamber further includes at least one duct extending therefrom and said at least one duct is coupled to said storage section and operating so that said duct provides gaseous communication from said second chamber to said storage section.

20. The inhaler of claim 19 wherein a drug is in a liquid or powder form in said tube which is further sealed with an overlay at its ends thereof.

21. The inhaler in claim 20 wherein said tube further comprises an aerosol nozzle at an end thereof.

22. The inhaler of claim 1 wherein Heliox or helium compressed gas is contained in the first and second chambers.

23. The inhaler of claim 1 further comprising a spacer disposed between said storage section and said mouthpiece, said spacer being operable to receive a drug cloud from said storage section and convey said drug cloud to said mouthpiece.

24. The inhaler of claim 23 wherein said spacer comprises:
    an input port hermetically coupled to said storage section; and
    an inhalation port door coupled to said mouthpiece, said inhalation port door and said input port operable to allow said spacer to be selectively hermetically sealed from an ambient environment around said spacer.

25. The inhaler of claim 23 wherein said spacer comprises a pressure port, said pressure port operable to selectively allow removal of gas within said spacer when said drug cloud is received by said spacer.

26. The inhaler of claim 23 wherein said spacer comprises a pressure/vacuum port, said pressure/vacuum port operable to selectively allow ambient air into said spacer when user inhales a drug cloud.

27. The inhaler of claim 23 wherein said spacing further comprises a scented receptacle.

28. The inhaler of claim 23 wherein said spacer comprises a plurality of shelves disposed therein, said shelves operable to facilitate laminar flow of a drug cloud through said spacer.

29. The inhaler of claim 1 further comprising a diffuser disposed between said storage section and said mouthpiece.

30. The inhaler of claim 29, wherein said diffuser comprises a plurality of shelves disposed therein, said shelves operable to facilitate laminar flow of said drug cloud through said diffuser.

31. An inhaler for introducing a drug into a user, said inhaler comprising:
    a first chamber having a compressed gas at a first pressure contained therein, said first chamber being substantially free of any drug;
    a second chamber in selective flow communication with said first chamber, said second chamber having a second compressed gas in which said second pressure being lower than the first pressure and said second chamber being substantially free of any drug, said first and second chambers cooperating so as to yield said second pressure of said compressed gas within said second chamber upon use of said inhaler;
    a means for delivering two different volumes of gas in successive applications from the second chamber;
    a venturi section coupled to said second chamber, said venturi section containing said drug and adapted for effectively receiving a portion of said compressed gas from said second chamber to aerosolize said drug to thereby produce a drug cloud;
    a mouthpiece coupled to said venturi section, and adapted to receive said drug cloud and convey said drug cloud to said user a first housing disposed within said first chamber; a second housing disposed within said second chamber having an opening therein; and a piston slidably disposed within said first and second housings.

32. The inhaler as claimed in claim 31, further comprising a drug reservoir coupled to said venturi.

33. The inhaler as claimed in claim 31, wherein said first or second compressed gas comprises helium or Heliox.

* * * * *